US008410053B2

(12) United States Patent
Bachovchin et al.

(10) Patent No.: US 8,410,053 B2
(45) Date of Patent: Apr. 2, 2013

(54) METHODS FOR TREATING AUTOIMMUNE DISORDERS, AND REAGENTS RELATED THERETO

(75) Inventors: William W. Bachovchin, Melrose, MA (US); Vijay K. Kuchroo, Newton, MA (US)

(73) Assignees: Trustees of Tufts College, Medford, MA (US); Brigham & Women's Hospital, Boston, MA (US)

( * ) Notice: Subject to any disclaimer, the term of this patent is extended or adjusted under 35 U.S.C. 154(b) by 895 days.

(21) Appl. No.: 10/496,627

(22) PCT Filed: Nov. 26, 2002

(86) PCT No.: PCT/US02/38347
§ 371 (c)(1),
(2), (4) Date: Nov. 15, 2004

(87) PCT Pub. No.: WO03/045228
PCT Pub. Date: Jun. 5, 2003

(65) Prior Publication Data
US 2005/0070459 A1   Mar. 31, 2005

Related U.S. Application Data

(60) Provisional application No. 60/333,691, filed on Nov. 26, 2001.

(51) Int. Cl.
*A61K 38/00* (2006.01)
(52) U.S. Cl. ..................................... 514/17.9
(58) Field of Classification Search .................. None
See application file for complete search history.

(56) References Cited

U.S. PATENT DOCUMENTS

| | | | |
|---|---|---|---|
| 4,522,752 A | 6/1985 | Sisto et al. | |
| 4,935,493 A | 6/1990 | Bachovchin et al. | |
| 5,061,811 A | 10/1991 | Pinori et al. | |
| 5,462,928 A | 10/1995 | Bachovchin et al. | |
| 5,580,979 A | 12/1996 | Bachovchin | |
| 5,631,224 A | 5/1997 | Efendic et al. | |
| 5,776,902 A | 7/1998 | Bachovchin | |
| 5,783,556 A | 7/1998 | Clark et al. | |
| 5,834,428 A | 11/1998 | Drucker | |
| 5,952,301 A | 9/1999 | Drucker | |
| 6,011,155 A | 1/2000 | Villhauer | |
| 6,258,597 B1 | 7/2001 | Bachovchin et al. | |
| 6,300,314 B1 | 10/2001 | Wallner et al. | |
| 6,355,614 B1 | 3/2002 | Wallner | |
| 6,703,238 B2 | 3/2004 | Bachovchin et al. | |
| 6,770,628 B2 | 8/2004 | Wallner et al. | |
| 6,803,357 B1 | 10/2004 | Bachovchin et al. | |
| 6,825,169 B1 | 11/2004 | Bachovchin et al. | |
| 6,890,898 B2 | 5/2005 | Bachovchin | |
| 6,890,904 B1 | 5/2005 | Wallner et al. | |
| 6,949,514 B2 | 9/2005 | Wallner et al. | |
| 6,979,697 B1 | 12/2005 | Wallner | |
| 7,157,429 B1 * | 1/2007 | Bachovchin et al. ............ 514/18 |
| 2003/0130517 A1 | 7/2003 | Yasuma et al. | |
| 2003/0153509 A1 | 8/2003 | Bachovchin et al. | |
| 2003/0158114 A1 | 8/2003 | Wallner et al. | |
| 2004/0077601 A1 | 4/2004 | Adams et al. | |
| 2004/0152192 A1 | 8/2004 | Bachovchin et al. | |
| 2004/0176307 A1 | 9/2004 | Bachovchin et al. | |
| 2004/0229820 A1 | 11/2004 | Bachovchin et al. | |
| 2005/0037976 A1 | 2/2005 | Wallner et al. | |
| 2005/0049177 A1 | 3/2005 | Bachovchin et al. | |
| 2005/0070482 A1 | 3/2005 | Bachovchin | |
| 2005/0084490 A1 | 4/2005 | Adams et al. | |
| 2005/0203027 A1 | 9/2005 | Bachovchin et al. | |
| 2005/0272703 A1 | 12/2005 | Wallner et al. | |
| 2006/0052310 A1 | 3/2006 | Wallner | |
| 2006/0063719 A1 | 3/2006 | Jesson et al. | |

FOREIGN PATENT DOCUMENTS

| | | |
|---|---|---|
| CA | 2 343 459 A1 | 10/2001 |
| DE | 196 16 486 | 10/1997 |
| WO | WO-89/03223 | 4/1989 |
| WO | WO 91/16339 A1 | 10/1991 |
| WO | WO-93/08259 | 4/1993 |
| WO | WO-95/15309 | 6/1995 |
| WO | WO-96/14857 | 5/1996 |
| WO | WO-96/39385 A1 | 12/1996 |
| WO | WO-97/40832 | 11/1997 |
| WO | WO-98/19998 | 5/1998 |
| WO | WO-98/25644 | 6/1998 |
| WO | WO 99/15183 * | 9/1998 |
| WO | WO 99/38501 A2 | 8/1999 |
| WO | WO 99/62914 A1 | 12/1999 |
| WO | WO-00/10549 | 3/2000 |
| WO | WO-01/14318 A2 | 3/2001 |

(Continued)

OTHER PUBLICATIONS

Reinhold D, Dipeptidyl peptidase IV (CD26): Role in T cell activation and autoimmune disease. Adv Exp Med Biol (2000);477:155-60.*
Davidson A.N. et al, "Autoimmune diseases," Engl J Med. Aug. 2, 2001;345(5):340-50.*
Tanaka S, et al "Suppression of arthritis by the inhibitors of dipeptidyl peptidase IV." Int J Immunopharmacol. Jan. 1997;19(1):15-24.*
Kubota, T. et al. "Involvement of dipeptidyl peptidase IV in an in vivo immune response." Clin. Exp. Immunol. 89: 192-197 (1992).
Flentke, G. R. et al. "Inhibition of dipeptidyl aminopeptidase IV(DP-IV) by Xaa-boroPro dipeptides and use of these inhibitors to examine the role of DP-IV in T-cell function." Proc. Natl. Acad. Sci USA 88: 1556-1559 (1991).
Kubota, T. et al. "Dipeptidyl peptidase IV (DP IV) activity in serum and on lymphocytes of MRL/Mp-*Ipr/Ipr* mice correlates with disease onset." Clin. Exp. Immunol. 96: 292-296 (1994).
English Translation of Official Action issued in corresponding Japanese application (Japanese Patent Application No. 2003-546737) mailed Jul. 28, 2009.

(Continued)

Primary Examiner — Thomas Heard
(74) Attorney, Agent, or Firm — Dana M. Gordon; Foley Hoag LLP

(57) ABSTRACT

The invention generally relates to improved methods for treatment or prophylaxis in animal subjects (including humans) of autoimmune disorders including Type I diabetes, septic shock, multiple sclerosis, inflammatory bowel disease (IBD) and Crohn's disease.

11 Claims, 6 Drawing Sheets

FOREIGN PATENT DOCUMENTS

| | | |
|---|---|---|
| WO | WO-01/34594 | 5/2001 |
| WO | WO 01/51641 A1 | 7/2001 |
| WO | WO-01/81337 | 11/2001 |
| WO | WO 01/89569 A1 | 11/2001 |

OTHER PUBLICATIONS

Bell et al., 1983, "Exon duplication and divergence in the human preproglucagon gene", Nature 304 (5924):368-71.

Conlon, 1988, "Proglucagon-derived peptides: nomenclature, biosynthetic relationships and physiological roles", Diabetolgia 31(8):563-6.

Coutts et al. Structure-Activity Relationships of Boronic Acid Inhibitors of Dipeptidyl Peptidase IV. I. Variation of the P2 Position of Xaa-boroPro Dipeptides. J. Med. Chem. 39, 2087-2094 (1996).

Deacon et al. Degradation of Glucagon-Like Peptide-1 by Human Plasma in Vitro Yields an N-Terminally Truncated Peptide that is a Major Endogenous Metabolite in Vivo. J. Clin. Endocrin. 83, 952-957 (1995).

Gutniak et al., 1992, "Antidiabetogenic effect of glucagon-like peptide-1 (7-36) amide in normal subjects and patients with diabetes mellitus", N Engl J Med 326(20):1316-22.

Holst, J. J. & Deacon, C.F. Inhibition of the Activity of Dipeptidyl-Peptidase IV as a Treatment for Type 2 Diabetes. Diabetes 47, 1663-1670 (1998).

Kawashima et al., 1990, "Pharmacological differentiation of presynaptic M1 muscarinic receptors modulating acetylcholine release from postsynaptic muscarinic receptors in guinea-pig ileum", Gen Pharmacol 21(1):17-21.

Kinder et al., 1985, "Acylamino boronic acids and difluoroborane analogues of amino acids: potent inhibitors of chymotrypsin and elastase", J Med Chem 28(12):1917-25.

Kubiak et al., 1994, "Metabolism or mouse growth hormone-releasing factor, mGRF(1-42)OH, and selected analogs from the bovine GRF series in mouse and bovine plasma in vitro", Pept Res 7(3):153-61.

Lund et al., 1982, "Pancreatic preproglucagon cDNA contains two glucagon-related coding sequences arranged in tandem", Proc Natl Acad Sci U S A 79(2):345-9.

Mentlein et al. Dipeptidyl-peptidase IV hydrolyses gastric inhibitory polypeptide, glucagons-like peptide-1(7-36)amide, peptide histidine methionine and is responsible for their degradation in human serum. Eur. J. Biochem. 214, 829-835 (1993).

Mojsov et al., 1986, "Preproglucagon gene expression in pancreas and intestine diversifies at the level of post-translational processing", J Biol Chem 261(25):11880-9.

Mojsov, 1992, "Structural requirements for biological activity of glucagon-like peptide-I", Int J Pept Protein Res 40(3-4):333-43.

Patzelt et al., 1979, "Identification and processing of proglucagon in pancreatic islets", Nature 282(5736):260-6.

Pospisilik, John A. et al. Metabolism of Glucagon by Dipeptidyl Peptidase IV (CD26). Regulatory Peptides 96, 133-141, 2001.

Schmidt et al., 1985, "Glucagon-like peptide-1 but not glucagon-like peptide-2 stimulates insulin release from isolated rat pancreatic islets", Diabetologia 28(9):704-7.

Stanely et al., 1989, "Repeated hypothalamic stimulation with neuropeptide Y increases daily carbohydrate and fat intake and body weight gain in female rats", Physiol Behav 46(2):173-7.

Wilding et al., 1992, "Increased neuropeptide Y content in individual hypothalamic nuclei, but not neuropeptide Y mRNA, in diet-induced obesity in rats", J Endocrinol 132(2):299-304.

Dupre, 1991, "Influences of the gut on the endocrine pancreas" The Endocrine Pancreas (Raven Press, New York) pp. 253-281.

Weir et al., 1989, "Glucagonlike peptide I (7-37) actions on endocrine pancrease", Diabetes 38(3):338-42.

Shue et al., 1987, "Amide bond surrogates: a general synthetic route to trans carbon-carbon double bond isosteres", Tetrahedron Letters 28:3225.

Radhakrishna et al., 1979, "New method for direct conversion of amides to amines", J Org Chem 44:1746.

Pederson et al. Improved Glucose Tolerance in Zucker Fatty Rats by Oral Administration of the Dipeptidyl Peptidase IV Inhibitor Isoleucine Thiazolidide. Diabetes 47, 1253-1258 (Aug. 1998).

Orskov et al., 1987, "Pancreatic and intestinal processing of proglucagon in man," Diabetologia 30(11):874-81.

Mojsov et al., 1987, "Insulinotropin: glucagon-like peptide I (7-37) co-encoded in the glucagon gene is a potent stimulator of insulin release in the perfused rat pancreas", J Clin Invest 79(2):616-9.

Mentlein et al. Proteolytic processing of neuropeptide Y and peptide YY by dipeptidyl peptidase IV. Regulatory Peptides 49, 133-144 (Dec. 10, 1993).

Matteson et al., 1984, "Synthesis and properties of pinanediol A-amino boronic acids", Organometallics 3:1284.

Lambrecht et al., 1989, "Pharmacology of hexahydro-difenidol, hexahydro-sila-difenidol and related selective muscarinic antagonists", Trends Pharmacol Sci 10(Suppl):60.

Kreymann et al., 1987, "Glucagon-like peptide-1 7-36: a physiological incretin in man", Lancet 2(8571):1300-4.

Kieffer et al. Degradation of Glucose-Dependent Insulinotropic Polypeptide and Truncated Glucagon-Like Peptide 1 in Vitro and in Vivo by Dipeptidyl Peptidase IV, Endocrin. 136, 3585-3596 (1995).

Hoist et al., 1987, "Truncated glucagon-like peptide I, an insulin-releasing hormone from the distal gut", FEBS Lett. 211(2):169-74.

Habener et al., 1991, "Biosyntesies of glucagon" The Endocrine Pancreas (Raven Press, New York) pp. 53-71.

Ebert et al., 1987, "Gastrointestinal peptides and insulin secretion", Diabetes Met. Rev. 3:1-26.

Deacon et al., 1995, "Both subcutaneously and intravenously administered glucagon-like peptide I are rapidly degraded from the NH2-terminus in type II diabetic patients and in healthy subjects", Diabetes 44(9):1126-31.

Coruzzi et al., 1989, "Gastric antisecretory activity of telenzepine, a new M1-selective muscarinic antagonist: comparison with pirenzepine", Arch Int Pharmacodyn Ther 302:232-41.

Bell et al., 1983, "Hamster preproglucagon contains the sequence of glucagon and two related peptides", Nature 302(5910):716-8.

Balkan et al. Improved insulin secretion and oral glucose tolerance after in vivo inhibition of DPP-IV in obese zucker rats. Diabetolgia Suppl. 40, A131 Abstract (1997).

Deacon et al. Diabetes. 1998. vol. 47, pp. 764-769.

Snow et al. "Studies on Proline Boronic Acid Dipeptide Inhibitors of Dipeptidyl Peptidase IV: Identification of a Cyclic Species Containing a B-N bond." J. Am. Chem.Soc. 116(24): 10860-10869 (1994).

Tanaka et al. "Suppression of Arthritis by the Inhibitors of Dipeptidyl Peptidase IV." Japanese Journal of Inflammation 18(3): 199-202 (1998).

\* cited by examiner

Synthesis Of Cyclohexylglycine boroAla

METHODS FOR TREATING AUTOIMMUNE DISORDERS, AND REAGENTS RELATED THERETO

CROSS-REFERENCE TO RELATED APPLICATIONS

This application is a national stage filing under 35 U.S.C. 371 of International Application PCT/US02/38347 filed Nov. 26, 2002, which claims priority from U.S. Application No. 60/333,691 filed Nov. 26, 2001, the specifications of each of which are hereby incorporated by reference in their entirety. International Application PCT/US02/38347 was published under PCT Article 21(2) in English.

GOVERNMENT SUPPORT

This invention was made with government support under NS035685 awarded by the National Institutes of Health. The government has certain rights in the invention.

BACKGROUND OF THE INVENTION

The immune system can normally distinguish "self" from "non-self". Some immune system cells (lymphocytes) become sensitized against "self" tissue cells, but are normally controlled by other lymphocytes. When the normal control process is disrupted, allowing lymphocytes to avoid suppression, or when there is an alteration in some body tissue so that it is no longer recognized by the immune system as "self", autoimmune disorders develop. The mechanisms that cause disrupted control or tissue alterations are not well known. One theory holds that various microorganisms and drugs may trigger some of these changes, particularly in people with genetic predisposition to autoimmune disorders. There are a number of autoimmune diseases including, for example, multiple sclerosis (MS), rheumatoid arthritis (RA), and Type I diabetes.

Type I diabetes is a progressive autoimmune disease, in which the beta cells that produce insulin are slowly destroyed by the body's own immune system. White blood cells called T lymphocytes produce immune factors called cytokines that attack and gradually destroy the beta cells of the pancreas. Important cytokines are interleukin-1-beta, tumor necrosis factor-alpha, and interferon-gamma. Specific proteins are also critical in the process. They include glutamic acid decarboxylase (GAD), insulin, and islet cell antigens. These proteins serve as autoantigens. That is, they trigger the self attack of the immune system on its body's own beta cells. It is unknown what first starts this cascade of immune events, but evidence suggests that both a genetic predisposition and environmental factors, such as a viral infection, are involved.

As a result of autoimmune diabetes, the pancreas produces little or no insulin, and insulin must be injected daily for the survival of the diabetic. Insulin, a hormone produced by the pancreas, is needed to convert sugar, starches and other food into glucose and to make it available to the body's cells for energy. In muscle, adipose (fat) and connective tissues, insulin facilitates the entry of glucose into the cells by an action on the cell membranes. The ingested glucose is normally converted in the liver to $CO_2$ and $H_2O$ (50%); to glycogen (5%); and to fat (30-40%), the latter being stored in fat depots. Fatty acids from the adipose tissues are circulated, returned to the liver for re-synthesis of triacylglycerol and metabolized to ketone bodies for utilization by the tissues. The fatty acids are also metabolized by other organs. Fat formation is a major pathway for carbohydrate utilization. The net effect of insulin is to promote the storage and use of carbohydrates, protein and fat.

Some complications arising from long-standing diabetes are vascular disease, microvascular disease, eye complications, diabetic nephropathy, diabetic neuropathy, diabetic foot problems, and skin and mucous membrane problems. The action of Type 1 diabetes is to cause hyperglycemia (elevated blood glucose concentration) and a tendency towards diabetic ketoacidosis (DKA). Currently treatment requires chronic administration of insulin. Sporadic or persistent incidence of hyperglycemia can be controlled by administering insulin. Uncontrolled hyperglycemia can further damage the cells of the pancreas which produce insulin (the β-islet cells) and in the long term create greater insulin deficiencies.

Type 1 diabetes (Insulin dependent diabetes mellitus, IDDM) represents 20% of all human diabetes, and is the most serious form of the disease, with highest morbidity an mortality. Up to 800,000 people in the US are estimated to have type 1 diabetes, with about 30,000 new cases diagnosed each year. In addition., the incidence of IDDM has been rising over the past few decades in certain regions of the US and some European countries, particularly in Finland and England.

Currently, oral sulfonylureas and insulin injections are the only two therapeutic agents available in the United States for treatment of Diabetes mellitus. Both agents have the potential for producing hypoglycemia as a side effect, reducing the blood glucose concentration to dangerous levels. There is no generally applicable and consistently effective means of maintaining an essentially normal fluctuation in glucose levels in DM. The resultant treatment attempts to minimize the risks of hypoglycemia while keeping the glucose levels below a target value. The drug regimen is combined with control of dietary intake of carbohydrates to keep glucose levels in control. However, to date, there has been no cure for many autoimmune disorders, including type 1 diabetes. Clearly, a strong need exists for new, more effective treatments for these diseases.

SUMMARY OF THE INVENTION

The invention generally relates to improved methods for treatment or prophylaxis in animal subjects (including humans) of autoimmune disorders including Type I diabetes, septic shock, multiple sclerosis, inflammatory bowel disease (IBD) and Crohn's disease.

One aspect of the invention relates to a method for treating a mammal having an autoimmune disease, such as Type I diabetes, septic shock, multiple sclerosis, IBD, or Crohn's disease, comprising administering to the mammal a dipeptidylpeptidase IV (DPIV) inhibitor, wherein administering the inhibitor induces immunosuppression and modulates the pharmacokinetics of polypeptide hormones required for tissue regeneration.

Figure 1:
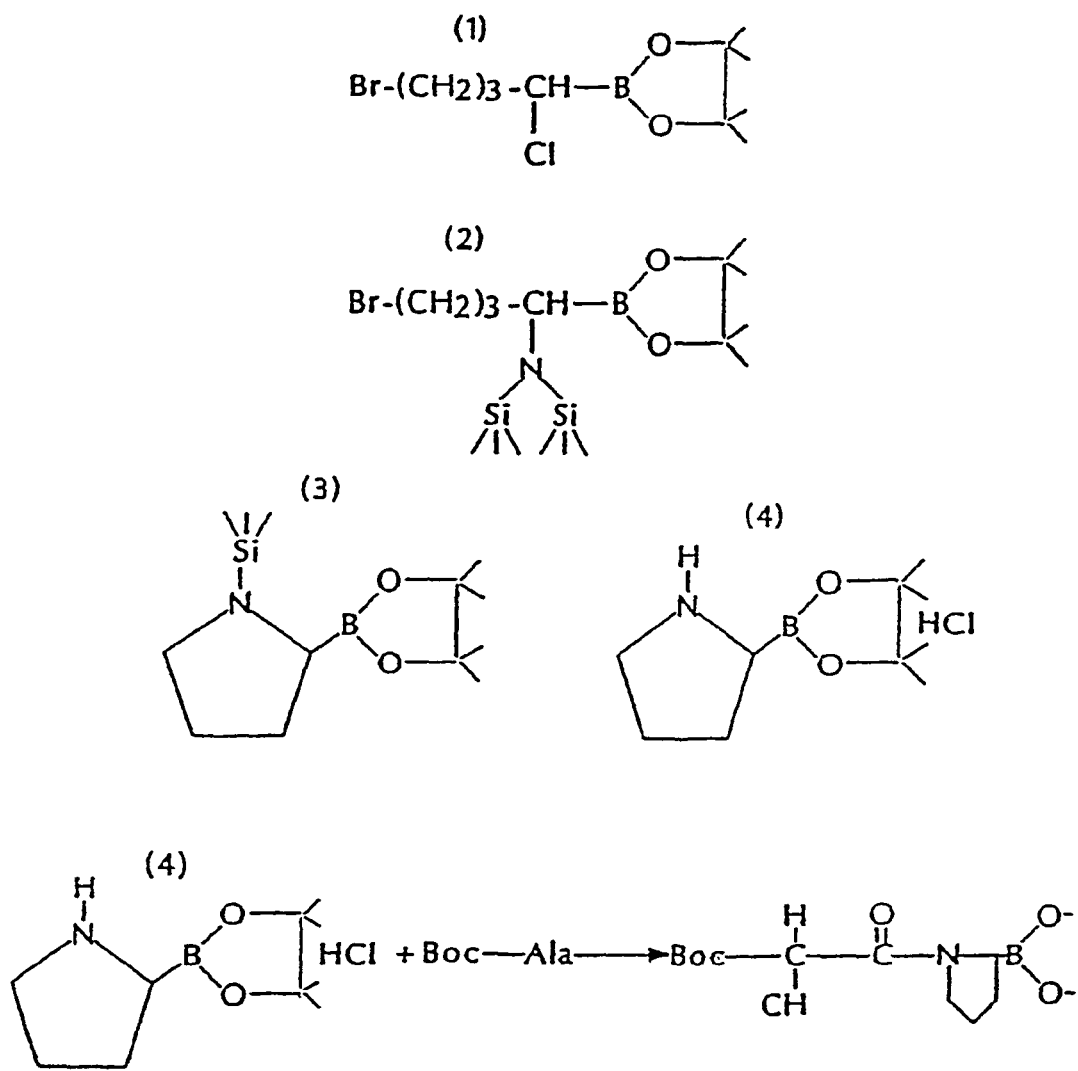
FIG. 1 is a diagrammatic representation of the synthesis of a boro-Pro compound.
Figure 2:
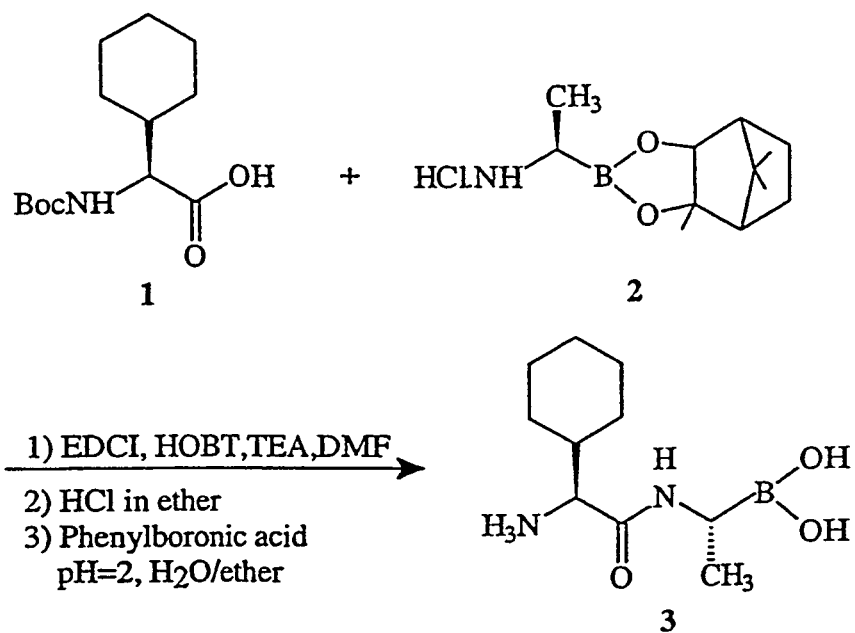
FIG. 2 is a diagrammatic representation of the synthesis of a Cyclohexylglycine-boro-Ala.
Figure 3:
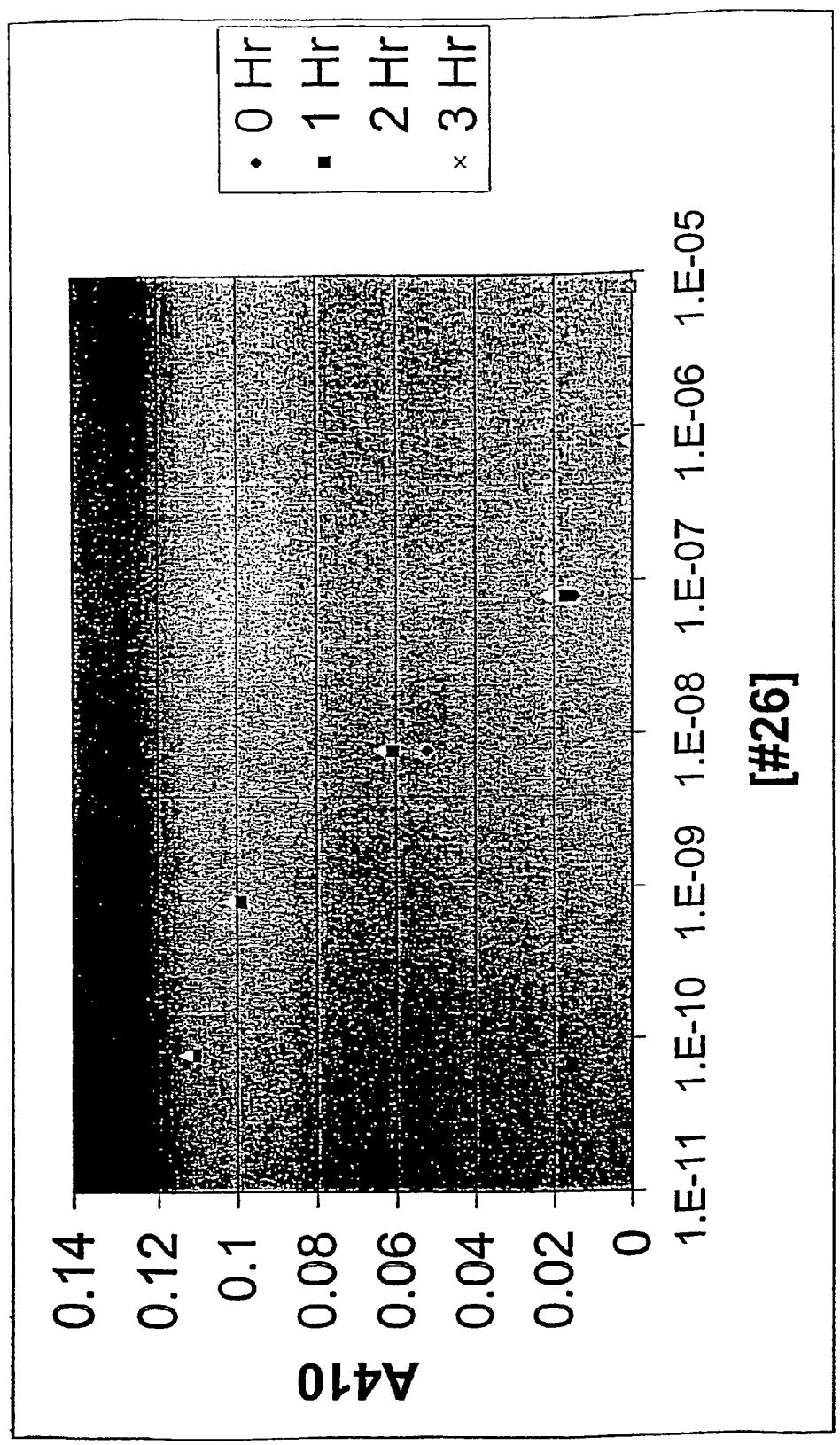
FIG. 3 is a time course of inactivation curve of Cyclohexylglycine-boro-Ala at pH 8.
Figure 4:
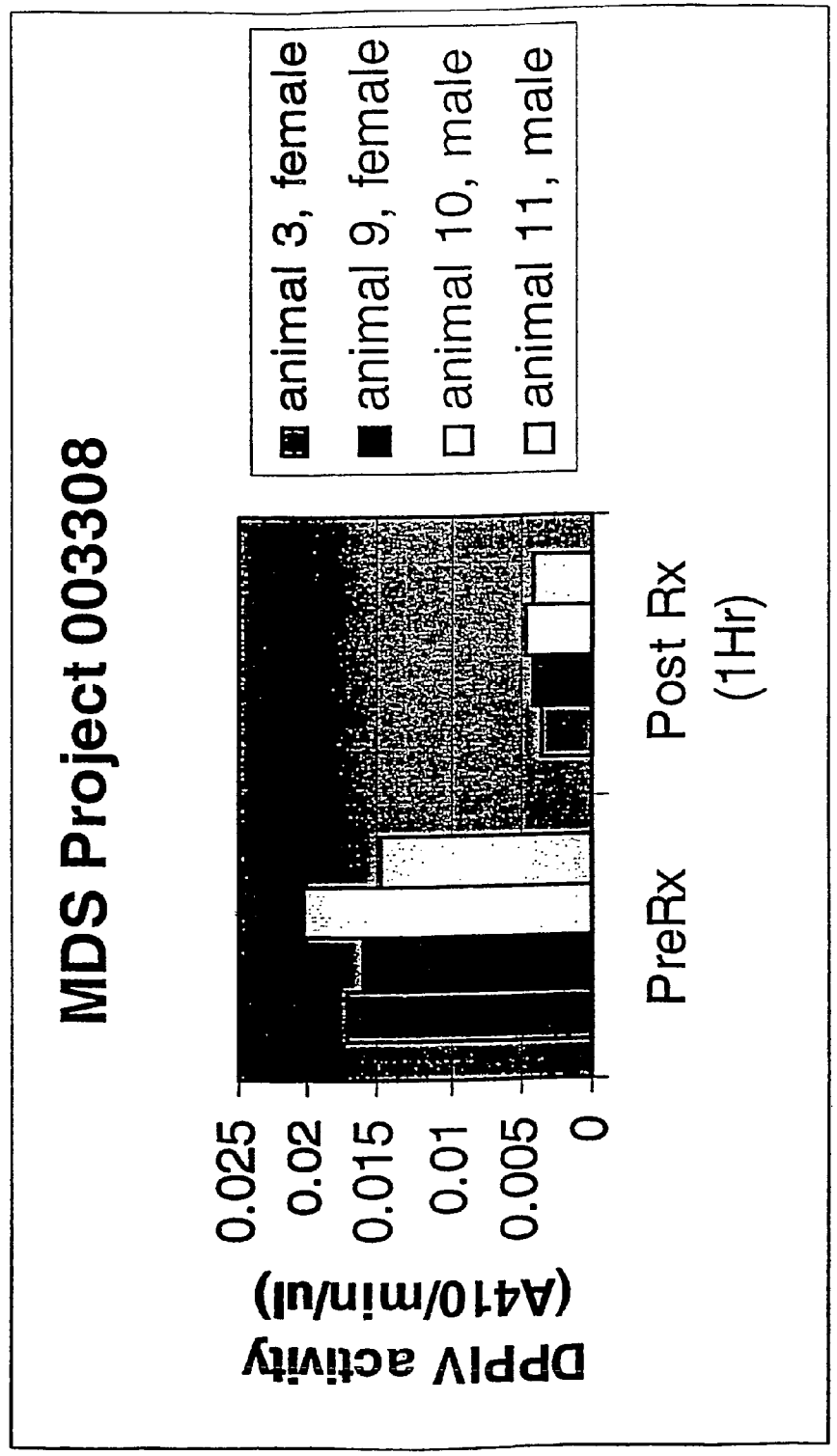
FIG. 4 is a bar graph illustrating DPPIV enzyme activity as measured from rat serum samples before and 1 hour after administration of Cyclohexylglycine-boro-Ala.

DETAILED DESCRIPTION OF THE INVENTION i. Overview of the Invention

The present invention provides methods and compositions generally to prevent, reduce, or eliminate autoimmune disorders, such as Type 1 diabetes, septic shock, multiple sclerosis, IBD or Crohn's disease in animals. As described in greater detail below, the subject method includes' the administration, to an animal, of a composition including one or more dipeptidylpeptidase inhibitors, especially inhibitors of the dipeptidylpeptidase IV (DPIV) enzyme or other enzyme of similar specificity, in an amount which modulates the pharmacokinetics of polypeptide hormones in a manner that produces tissue regeneration (e.g., such as may be manifest in an increase in tissue mass). While not being bound by any particular theory, it may be useful to deliver an amount of DPIV inhibitor sufficient to suppress an autoimmune component of the disease (such as a reduce a cellular and/or humoral response against the target tissue). Other immunosuppressive agents can be administered conjointly.

For instance, in certain embodiments the method involves administration of a DPIV inhibitor, preferably at a predetermined time(s) during a 24-hour period, in an amount effective to improve one or more aberrant indices associated with Type 1 diabetes, septic shock, multiple sclerosis, IBD or Crohn's disease.

The present invention provides methods and compositions for regeneration of tissues damaged or destroyed as a result of autoimmune diseases by altering the half-life of a variety of different polypeptide hormones through inhibiting the proteolysis of one or more peptide hormones by DPIV or some other proteolytic activity.

The subject method can be used to increase the half-life of proglucagon-derived peptides including glucagon, glucagon-like peptide-1 (GLP-1), glucagon-like peptide-2 (GLP-2, PG 126-158), glicentin (corresponding to PG 1-69), oxyntomodulin (PG 33-69), glicentin-related pancreatic polypeptide (GRPP, PG 1-30), intervening peptide-2 (IP-2, PG 111-122amide), glucose-dependent insulinotropic peptides, vasoactive intestinal polypeptide (VIP), vasostatin I and II, peptide histidine methionine (PHM), peptide histidine isoleucine (PHI), secretin, gastric inhibitory peptide, gastrin-releasing peptide (GRP), growth hormone-releasing hormone (GHRH), helospectin, helodermin, pituitary adenylate cyclase-activating peptide (PACAP, PACAP 27, and PACAP 38), and PACAP-related peptide (PRP), as well as calcitonin and secretin.

For instance, autoimmune (Type 1) diabetes leads to apoptotic destruction of β-pancreatic islets responsible for insulin secretion. Polypeptide hormones, such as exendin-4, an analog of glucagon-like peptide 1 (GLP-1), have been shown to stimulate the regeneration of the pancreas and expansion of β-cells mass by processes of both neogenesis and proliferation of β-cells. Support for β-cell neogenesis being a direct effect of the exendin-4 comes from the finding that duct cells expressed GLP-1 receptor, both at the mRNA and protein levels. (Xu et. al. (1999) Diabetes 48:2270-2276). Thus, modulation of plasma half-life of GLP-1 and analogs thereof hold promise in a novel therapy to stimulate β-cell growth, and differentiation when administered to diabetic individuals with reduced β-cell mass.

In addition, GLP-1 and the longer acting GLP-1 agonist exendin-4 stimulate the expression of the IDX-1 homeodomain protein in the pancreas when administered to mice. Expression of both immunoreactive IDX-1 and β-galactosidase expressed from LacZ reporter transgene driven by the IDX-1 promoter occurs in the pancreatic ducts and the exocrine pancreas. It is also known that IDX-1 is required for the growth of the pancreas and that the epithelium of the pancreatic ducts and the centrolobular terminal ducts in the acinar tissue are the source of the differentiation of new β-cells (β-cell neogenesis). (Stoffers et al (2000) Diabetes 49:741-748). Thus, modulation of plasma half-life of GLP-1 and analogs thereof similarly hold promise in a novel therapy to stimulate β-cell neogenesis.

Furthermore, the activation of inducible nitric oxide synthase (INOS) by inflammatory cytokines is considered a mediator of destruction in β-cells. Recent findings showed that the neuropeptide pituitary adenyl cyclase-activating polypeptide (PACAP), whose distribution was identified in pancreatic neurons, inhibited nitric oxide (NO) production in cytokine-activated macrophages. (Seldya (2000) Biochem Biophys Res Comm (2000) 278(1):211-216) Therefore, modulation of half-life of PACAP and analogs thereof may be useful in treatment of Type 1 diabetes.

GLP-2, for example, has been identified as a factor responsible for inducing proliferation of intestinal epithelium. See, for example, Druclcer et al. (1996) PNAS 93:7911. The subject method can be used as part of a regimen for treating injury, inflammation, or resection of intestinal tissue, e.g., where enhanced growth and repair of the intestinal mucosal epithelial is desired. Thus modulation of half-life of GPL-2 and analogs thereof hold promise for the treatment of gut-related autoimmune diseases, such as, for example, inflammatory bowel disease (IBD).

Rheumatoid arthritis (RA) is a chronic and debilitating autoimmune disease of unknown ethiology, characterized by chronic inflammation in the joints and subsequent destruction of the cartilage and bone. Neuropeptide vasoactive intestinal peptide (VIP) has been shown to significantly reduce incidence and severity of arthritis, completely abrogating joint swelling and destruction of cartilage and bode. (Delgado (2001) Nat Med 7(5) 563-568) Consequently modulation of half-life of VIP and analogs thereof holds promise for the treatment of rheumatoid arthritis. In addition, VIP itself as well as more stable VIP derived agents, have been used or proposed as efficient therapeutic treatments of several autoimmune disorders, such as septic shock, multiple sclerosis, Crohn's disease, and autoimmune diabetes. (Gomariz (2001) Curr Pharm Des 7(2):89-111).

Additionally, the subject method can be used to alter the pharmacokinetics of Peptide YY (PYY) and neuropeptide Y (NPY), both members of the pancreatic polypeptide family, as DPIV has been implicated in the processing of those peptides in a manner which alters receptor selectivity.

DPIV has also been implicated in the metabolism and inactivation of growth hormone-releasing factor (GHRF). GHRF is a member of the family of homologous peptides that includes glucagon, secretin, vasoactive intestinal peptide (VIP), peptide histidine isoleucine (PHI), pituitary adenylate cyclase activating peptide (PACAP), gastric inhibitory peptide (GIP) and helodermin. Kubiak et al. (1994) Peptide Res 7:153. GHRF is secreted by the hypothalamus, and stimulates the release of growth hormone (GH) from the anterior pituitary. Thus, the subject method can be used to improve clinical therapy for certain growth hormone deficient children, and in clinical therapy of adults to improve nutrition and to alter body composition (muscle vs. fat). The subject method can also be used in veterinary practice, for example, to develop higher yield milk production and higher yield, leaner livestock.

Additional other autoimmune diseases and conditions that may be treated with the methods of the present invention are: systemic lupus erythematosus (SLE), immunovasculitis, myasthenia gravis, acute immunological arthritis, Hashimoto's thyroiditis, Grave's disease, rheumatoid synovitis, hereditary angioedema, hyperacute allograft rejection, xenograft rejection, infectious disease and sepsis, endotoxemia, scleroderma, glomerulonephritis, HIV infection, multiple sclerosis, atrophic gastritis, pancreatitis, allergic encephalomyelitis, thyroxicosis, sympathetic ophthalmia, allergic reactions, multiple organ failure, allergic reactions, bullous diseases, urticaria, cryoglobulinemia, renal cortical necrosis, transplant organ reperfusion, post-ischemic reperfusion conditions, lupus nephritis, Crohn's disease, dermatomyositis, proliferative nephritis, type II collagen-induced arthritis, Bahcet's syndrome, Sjogren's syndrome, thermal injury, preeclampsia, thyroiditis, acute gouty arthritis, primary biliary cirrhosis inflammation, cranial nerve damage in meningitis, renal ischemia, anaphylaxis, and bowel inflammation.

In general, the inhibitors of the subject method will be small molecules, e.g., with molecular weights less than 7500 amu, preferably less than 5000 amu, and even more preferably less than 2000 amu and even 1000 amu. In preferred embodiments, the inhibitors will be orally active.

In preferred embodiments, a DPIV inhibitor of the present invention has a Ki for DPIV inhibition of 1.0 nM or less, more preferably of 0.1 nM or less, and even more preferably of 0.01 nM or less. Indeed, inhibitors with Ki values in the picomolar and even femtamolar range are contemplated.

Preferably, the compounds utilized in the subject method will have an EC50 for the desired biological effect, such as for example, increase in the plasma half-life of a peptide hormone that promotes tissue regeneration in the micromolar or less range more preferably in the nanomolar or less range and even more preferably in the picomolar or femtomolar range.

In certain embodiments, the subject inhibitors are peptidyl compounds (including peptidomimetics) which are optimized, e.g., generally by selection of the Cα substituents, for the substrate specificity of the targeted proteolytic activity. These peptidyl compounds will include a functional group, such as in place of the scissile peptide bond, which facilitates inhibition of a serine-, cysteine- or aspartate-type protease, as appropriate. For example, the inhibitor can be a peptidyl α-diketone or a peptidyl α-keto ester, a peptide haloalkylketone, a peptide sulfonyl fluoride, a peptidyl boronate, a peptide epoxide, a peptidyl diazomethanes, a peptidyl phosphonate, isocoumarins, benzoxazin-4-ones, carbamates, isocyantes, isatoic anhydrides or the like. Such functional groups have bee provided in other protease inhibitors, and general routes for their synthesis are known. See, for example, Angelastro et al., *J. Med Chem.* 33:11-13 (1990); Bey et al., EPO 363,284; Bey et al., EPO 364,344; Grubb et al., WO 88/10266; Higuchi et al., EPO 393,457; Ewoldt et al., *Molecular Immunology* 29(6):713-721 (1992); Hernandez et al., *Journal of Medicinal Chemistry* 35(6): 1121-1129 (1992); Vlasak et al., *J Virology* 63(5):2056-2062 (1989); Hudig et al., *J Immunol* 147(4):1360-1368 (1991); Odake et al., *Biochemistry* 30(8):2217-2227 (1991); Vijayalakshmi et al., *Biochemistry* 30(8):2175-2183 (1991); Kam et al., *Thrombosis and Haemostasis* 64(1):133-137 (1990); Powers et al., *J Cell Biochem* 39(1):33-46 (1989); Powers et al., Proteinase Inhibitors, Barrett et al., Eds., Elsevier, pp. 55-152 (1986); Powers et al., *Biochemistry* 29(12):3108-3118 (1990); Oweida et al., *Thrombosis Research* 58(2):391-397 (1990); Hudig et al., *Molecular Immunology* 26(8):793-798 (1989); Orlowski et al., *Archives of Biochemistry and Biophysics* 269(1):125-136 (1989); Zunino et al., *Biochimica et Biophysica Acta.* 967(3):331-340 (1988); Kam et al., *Biochemistry* 27(7):2547-2557 (1988); Parkes et al., *Biochem J.* 230:509-516 (1985); Green et al., *J. Biol. Chem.* 256:1923-1928 (1981); Angliker et al., *Biochem. J.* 241:871-875 (1987); Puri et al., *Arch. Biochem. Biophys.* 27:346-358 (1989); Hanada et al., Proteinase Inhibitors: Medical and Biological Aspects, Katunuma et al., Eds., Springer-Verlag pp. 25-36 (1983); Kajiwara et al., *Biochem. Int.* 15:935-944 (1987); Rao et al., *Thromb. Res.* 47:635-637 (1987); Tsujinaka et al., *Biochem. Biophys. Res. Commun.* 153:1201-1208 (1988)). See also U.S. Patents Bachovchin et al. U.S. Pat. No. 4,935,493; Bachovchin et al. U.S. Pat. No. 5,462,928; Powers et al. U.S. Pat. No. 5,543,396; Hanko et al. U.S. Pat. No. 5,296,604; and the PCT publication of Ferring PCT/GB94/02615.

In other embodiments, the inhibitor is a non-peptidyl compound, e.g., which can be identified by such drug screening assays as described herein. These inhibitors can be, merely to illustrate, synthetic organic compounds, natural products, nucleic acids or carbohydrates.

A representative class of compounds for use in the method of the present invention are represented by the general formula (as described in the PCT application No. PCT/US99/02294, which is incorporated herein by reference):

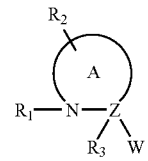

wherein

A represents a 4-8-membered heterocycle including the N and the Cα carbon;

Z represents C or N;

W represents a functional group which reacts with an active site residue of the targeted protease, as for example, —CN, —CH=NR$_5$,

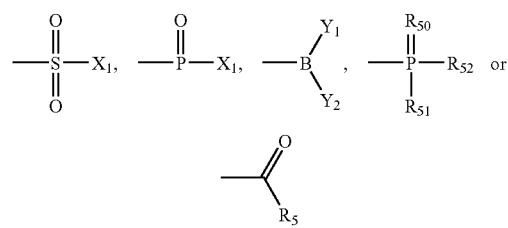

R$_1$ represents a C-terminally linked amino acid residue or amino acid analog, or a C-terminally linked peptide or peptide analog, or an amino-protecting group, or

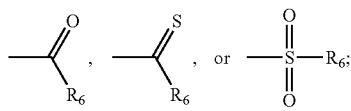

$R_2$ is absent or represents one or more substitutions to the ring A, each of which can independently be a halogen, a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, a nitro, an azido, a sulfate, a sulfonate, a sulfonamido, —$(CH_2)_m$—$R_7$, —$(CH_2)_m$—OH, —$(CH_2)_m$—O-lower alkyl, —$(CH_2)_m$—O-lower alkenyl, —$(CH_2)_n$—O—$(CH_2)_m$—$R_7$, —$(CH_2)_m$—SH, —$(CH_2)_m$—S-lower alkyl, —$(CH_2)_m$—S-lower alkenyl, —$(CH_2)_n$—S—$(CH_2)_m$—$R_7$;

if X is N, $R_3$ represents hydrogen, if X is C, $R_3$ represents hydrogen or a halogen, a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, a nitro, an azido, a sulfate, a sulfonate, a sulfonamido, —$(CH_2)_m$—$R_7$, —$(CH_2)_m$—OH, —$(CH_2)_m$—O-lower alkyl, —$(CH_2)_m$—O-lower alkenyl, —$(CH_2)_n$—O—$(CH_2)_m$—$R_7$, —$(CH_2)_m$—SH, —$(CH_2)_m$—S-lower alkyl, —$(CH_2)_m$—S-lower alkenyl, —$(CH_2)_n$—S—$(CH_2)_m$—$R_7$;

$R_5$ represents H, an alkyl, an alkenyl, an alkynyl, —$C(X_1)(X_2)X_3$, —$(CH_2)m$-$R_7$, —$(CH_2)n$-OH, —$(CH_2)n$-O-alkyl, —$(CH_2)n$-O-alkenyl, —$(CH_2)n$-O-alkynyl, —$(CH_2)n$-O—$(CH_2)m$-$R_7$, —$(CH_2)n$-SH, —$(CH_2)n$-S-alkyl, —$(CH_2)n$-S-alkenyl, —$(CH_2)n$-S-alkynyl, —$(CH_2)n$-S—$(CH_2)m$-$R_7$, —$C(O)C(O)NH_2$, —$C(O)C(O)OR'_7$;

$R_6$ represents hydrogen, a halogen, a alkyl, a alkenyl, a alkynyl, an aryl, —$(CH_2)_m$—$R_7$, —$(CH_2)_m$—OH, —$(CH_2)_m$—O-alkyl, —$(CH_2)_m$—O-alkenyl, —$(CH_2)_m$—O-alkynyl, $(CH_2)_m$—O—$(CH_2)_m$—$R_7$, $(CH_2)_m$—SH, —$(CH_2)_m$—S-alkyl, —$(CH_2)_m$—S-alkenyl, —$(CH_2)_m$—S-alkynyl, —$(CH_2)_m$—S—$(CH_2)_m$—$R_7$,

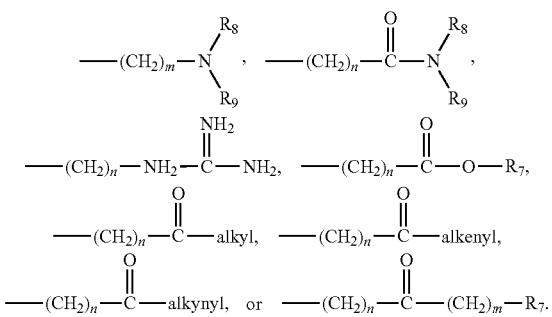

$R_7$ represents, independently for each occurrence, a substituted or unsubstituted aryl, aralkyl, cycloalkyl, cycloalkenyl, or heterocycle;

$R'_7$ represents, independently for each occurrence, hydrogen, or a substituted or unsubstituted alkyl, alkenyl, aryl, aralkyl, cycloalkyl, cycloalkenyl, or heterocycle;

$Y_1$ and $Y_2$ can, independently, be OH, or a group capable of being hydrolyzed to a hydroxyl group, including cyclic derivatives where $Y_1$ and $Y_2$ taken together form a ring having from 5 to 8 atoms in the ring structure (such as pinacol or the like);

$R_{50}$ represents O or S;

$R_{51}$ represents $N_3$, $SH_2$, $NH_2$, $NO_2$ or $OR'_7$;

$R_{52}$ represents hydrogen, a lower alkyl, an amine, $OR'_7$, or a pharmaceutically acceptable salt, or $R_{51}$ and $R_{52}$ taken together with the phosphorous atom to which they are attached complete a heterocyclic ring having from 5 to 8 atoms in the ring structure $X_1$ represents a halogen;

$X_2$ and $X_3$ each independently represent a hydrogen or a halogen;

m is zero or an integer in the range of 1 to 8; and n is an integer in the range of 1 to 8.

In preferred embodiments, the ring A is a 5, 6 or 7 membered ring, e.g., represented by the formula

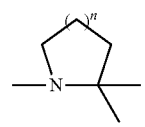

and more preferably a 5- or 6-membered ring. The ring may, optionally, be further substituted.

In preferred embodiments, W represents

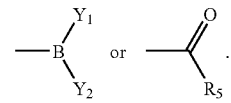

In preferred embodiments, $R_1$ is

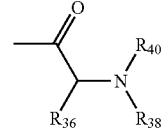

wherein $R_{36}$ is a small hydrophobic group, e.g., a lower alkyl or a halogen and $R_{38}$ is hydrogen, or, $R_{36}$ and $R_{37}$ together form a 4-7-membered heterocycle including the N and the Cα carbon, as defined for A above; and $R_{40}$ represents a C-terminally linked amino acid residue or amino acid analog, or a C-terminally linked peptide or peptide analog, or an amino-protecting group.

In preferred embodiments, $R_2$ is absent, or represents a small hydrophobic group such as a lower alkyl or a halogen.

In preferred embodiments, $R_3$ is a hydrogen, or a small hydrophobic group such as a lower alkyl or a halogen.

In preferred embodiments, $R_5$ is a hydrogen, or a halogenated lower alkyl.

In preferred embodiments, $X_1$ is a fluorine, and $X_2$ and $X_3$, if halogens, are fluorine.

Also deemed as equivalents are any compounds which can be hydrolytically converted into any of the aforementioned compounds including boronic acid esters and halides, and carbonyl equivalents including acetals, hemiacetals, ketals, and hemiketals, and cyclic dipeptide analogs.

Longer peptide sequences are needed for the inhibition of certain proteases and improve the specificity of the inhibition in some cases.

In preferred embodiments, the subject method utilizes, as a DPIV inhibitor, a boronic acid analogs of an amino acid. For example, the present invention contemplates the use of boroprolyl derivatives in the subject method. Exemplary boronic acid derived inhibitors of the present invention are represented by the general formula:

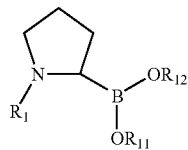

wherein $R_1$ represents a C-terminally linked amino acid residue or amino acid analog, or a C-terminally linked peptide or peptide analog, or an amino-protecting group, or

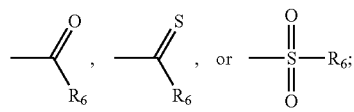

$R_6$ represents hydrogen, a halogen, an alkyl, an alkenyl, an alkynyl, an aryl, —$(CH_2)_m$—$R_7$, —$(CH_2)_m$—OH, —$(CH_2)_m$—O-alkyl, —$(CH_2)_m$—O-alkenyl, —$(CH_2)_m$—O-alkynyl, $(CH_2)_m$—O—$(CH_2)_m$—$R_7$, $(CH_2)_m$—SH, —$(CH_2)_m$—S-alkyl, —$(CH_2)_m$—S-alkenyl, —$(CH_2)_m$—S-alkynyl, —$(CH_2)_m$—S—$(CH_2)_m$—$R_7$,

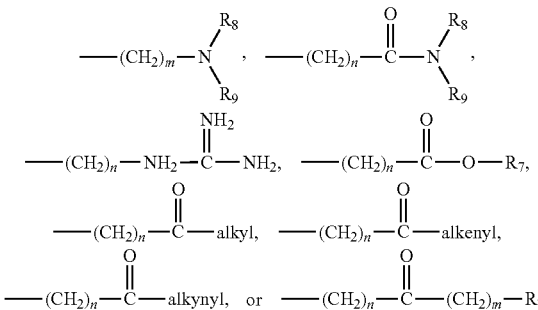

$R_7$ represents an aryl, a cycloalkyl, a cycloalkenyl, or a heterocycle;

$R_8$ and $R_9$ each independently represent hydrogen, alkyl, alkenyl, —$(CH_2)_m$—$R_7$, —C(=O)-alkyl, —C(=O)-alkenyl, —C(=O)-alkynyl, —C(=O)—$(CH_2)_m$—$R_7$, or $R_8$ and $R_9$ taken together with the N atom to which they are attached complete a heterocyclic ring having from 4 to 8 atoms in the ring structure;

$R_{11}$ and $R_{12}$ each independently represent hydrogen, a alkyl, or a pharmaceutically acceptable salt, or $R_{11}$ and $R_{12}$ taken together with the O—B—O atoms to which they are attached complete a heterocyclic ring having from 5 to 8 atoms in the ring structure;

m is zero or an integer in the range of 1 to 8; and n is an integer in the range of 1 to 8.

In other embodiments, the subject DPIV inhibitors include an aldehyde analogs of proline or prolyl derivatives. Exemplary aldehyde-derived inhibitors of the present invention are represented by the general formula:

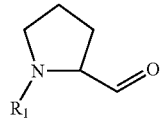

wherein $R_1$ represents a C-terminally linked amino acid residue or amino acid analog, or a C-terminally linked peptide or peptide analog, or an amino-protecting group, or

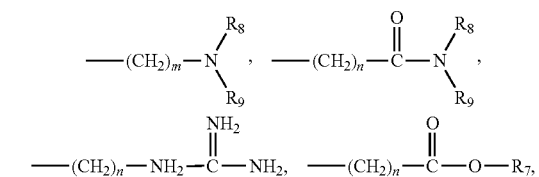

$R_6$ represents hydrogen, a halogen, an alkyl, an alkenyl, an alkynyl, an aryl, —$(CH_2)_m$—$R_7$, —$(CH_2)_m$—OH, —$(CH_2)_m$—O-alkyl, —$(CH_2)_m$—O-alkenyl, —$(CH_2)_m$—O-alkynyl, $(CH_2)_m$—$(CH_2)_m$—$R_7$, —$(CH_2)_m$—SH, —$(CH_2)_m$—S-alkyl, —$(CH_2)_m$—S-alkenyl, —$(CH_2)_m$—S-alkynyl, or —$(CH_2)_m$—S—$(CH_2)_m$—$R_7$,

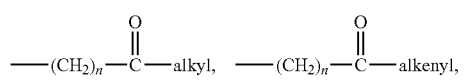

$R_7$ represents an aryl, a cycloalkyl, a cycloalkenyl, or a heterocycle;

$R_8$ and $R_9$ each independently represent hydrogen, alkyl, alkenyl, —$(CH_2)_m$—$R_7$, —C(=O)-alkyl, —C(=O)-alkenyl, —C(=O)-alkynyl, —C(=O)—$(CH_2)_m$—$R_7$, or $R_8$ and $R_9$ taken together with the N atom to which they are attached complete a heterocyclic ring having from 4 to 8 atoms in the ring structure; and m is zero or an integer in the range of 1 to 8; and n is an integer in the range of 1 to 8.

In yet further embodiments, the subject DPIV inhibitors are halo-methyl ketone analogs of an amino acid. Exemplary inhibitors of this class include compounds represented by the general formula:

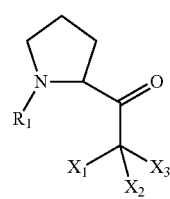

wherein $R_1$ represents a C-terminally linked amino acid residue or amino acid analog, or a C-terminally linked peptide or peptide analog, or an amino-protecting group, or

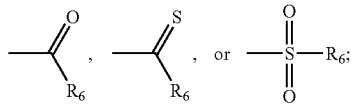

$R_6$ represents hydrogen, a halogen, an alkyl, an alkenyl, an alkynyl, an aryl, —(CH$_2$)$_m$—R$_7$, —(CH$_2$)$_m$—OH, —(CH$_2$)$_m$—O-alkyl, —(CH$_2$)$_m$—O-alkenyl, —(CH$_2$)$_m$—O-alkynyl, (CH$_2$)$_m$—O—(CH$_2$)$_m$—R$_7$, —(CH$_2$)$_m$—SH, —(CH$_2$)$_m$—S-alkyl, —(CH$_2$)$_m$—S-alkenyl, —(CH$_2$)$_m$—S-alkynyl, or —(CH$_2$)$_m$—S—(CH$_2$)$_m$—R$_7$,

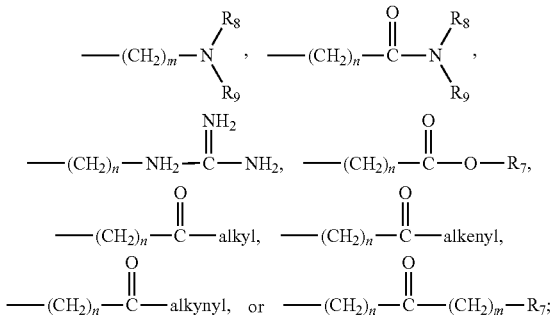

$R_7$ represents an aryl, a cycloalkyl, a cycloalkenyl, or a heterocycle;

$R_8$ and $R_9$ each independently represent hydrogen, alkyl, alkenyl, —(CH$_2$)$_m$—R$_7$, —C(=O)-alkyl, —C(=O)-alkenyl, —C(=O)-alkynyl, —C(=O)—(CH$_2$)$_m$—R$_7$, or $R_8$ and $R_9$ taken together with the N atom to which they are attached complete a heterocyclic ring having from 4 to 8 atoms in the ring structure;

$X_1$, $X_2$ and $X_3$ each represent a hydrogen or a halogen; and m is zero or an integer in the range of 1 to 8; and n is an integer in the range of 1 to 8.

In preferred embodiments, the DPIV inhibitor is a peptide or peptidomimetic including a prolyl group or analog thereof in the P1 specificity position, and a nonpolar amino acid in the P2 specificity position, e.g., a nonpolar amino acid such as alanine, leucine, isoleucine, valine, proline, phenylalanine, tryptophan or methionine, or an analog thereof. For example, the DPIV inhibitor may include an Ala-Pro or Pro-Pro dipeptide sequence or equivalent thereof, and be represented in the general formulas:

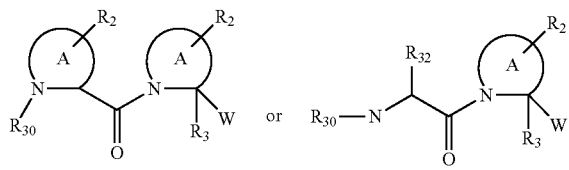

In preferred embodiments, the ring A is a 5-, 6-, or 7-membered ring, e.g., represented by the formula

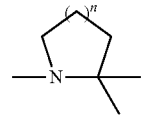

In preferred embodiments, $R_{32}$ is a small hydrophobic group, e.g., a lower alkyl or a halogen.

In preferred embodiments, $R_{30}$ represents a C-terminally linked amino acid residue or amino acid analog, or a C-terminally linked peptide or peptide analog, or an amino-protecting group.

In preferred embodiments, $R_2$ is absent, or represents a small hydrophobic group such as a lower alkyl or a halogen.

In preferred embodiments, $R_3$ is a hydrogen, or a small hydrophobic group such as a lower alkyl or a halogen.

Another representative class of compounds for use in the subject method include peptide and peptidomimetics of (D)-Ala-(L)-Ala, e.g., preserving the diasteromeric orientation of the substituents. Such inhibitors include compounds represented by the general formula:

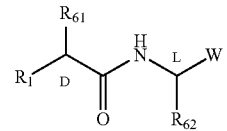

wherein

W represents a functional group which reacts with an active site residue of the targeted protease, as for example, —CN, —CH=NR$_5$,

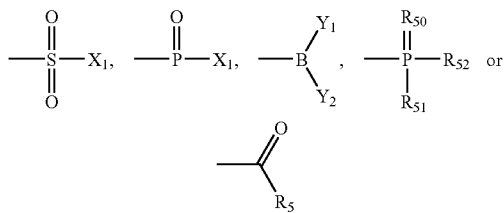

$R_1$ represents a C-terminally linked amino acid residue or amino acid analog, or a C-terminally linked peptide or peptide analog, or an amino-protecting group, or

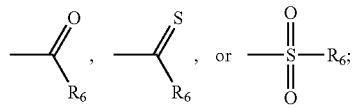

$R_3$ represents hydrogen or a halogen, a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, a nitro, an azido, a sulfate, a sulfonate, a sulfonamido, —(CH$_2$)$_m$—R$_7$, —(CH$_2$)$_m$—OH, —(CH$_2$)$_m$—O-lower alkyl, —(CH$_2$)$_m$—O-lower alkenyl, —(CH$_2$)$_n$—O—(CH$_2$)$_m$—R$_7$, —(CH$_2$)$_m$—SH, —(CH$_2$)$_m$—S-lower alkyl, —(CH$_2$)$_m$—S-lower alkenyl, —(CH$_2$)$_n$—S—(CH$_2$)$_m$—R$_7$;

$R_5$ represents H, an alkyl, an alkenyl, an alkynyl, —C($X_1$)($X_2$)$X_3$, —($CH_2$)m-$R_7$, —($CH_2$)n-OH, —($CH_2$)n-O-alkyl, —($CH_2$)n-O-alkenyl, —($CH_2$)n-O-alkynyl, —($CH_2$)n-O—($CH_2$)m-$R_7$, —($CH_2$)n-SH, —($CH_2$)n-S-alkyl, —($CH_2$)n-S-alkenyl, —($CH_2$)n-S-alkynyl, —($CH_2$)n-S—($CH_2$)m-$R_7$, —C(O)C(O)$NH_2$, —C(O)C(O)O$R'_7$;

$R_6$ represents hydrogen, a halogen, a alkyl, a alkenyl, a alkynyl, an aryl, —($CH_2$)$_m$—$R_7$, —($CH_2$)$_m$—OH, —($CH_2$)$_m$—O-alkyl, —($CH_2$)$_m$—O-alkenyl, —($CH_2$)$_m$—O-alkynyl, —($CH_2$)$_m$—O—($CH_2$)$_m$—$R_7$, —($CH_2$)$_m$—SH, —($CH_2$)$_m$—S-alkyl, —($CH_2$)$_m$—S-alkenyl, —($CH_2$)$_m$—S-alkynyl, —($CH_2$)$_m$—S—($CH_2$)$_m$—$R_7$,

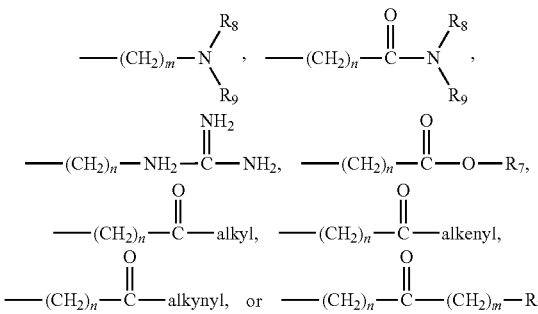

$R_7$ represents, for each occurrence, a substituted or unsubstituted aryl, aralkyl, cycloalkyl, cycloalkenyl, or heterocycle;

$R'_7$ represents, for each occurrence, hydrogen, or a substituted or unsubstituted alkyl, alkenyl, aryl, aralkyl, cycloalkyl, cycloalkenyl, or heterocycle;

$R_{61}$ and $R_{62}$, indepedently, represent small hydrophobic groups;

$Y_1$ and $Y_2$, independently, are OH, or a group capable of being hydrolyzed to a hydroxyl group, including cyclic derivatives where $Y_1$ and $Y_2$ taken together form a ring having from 5 to 8 atoms in the ring structure (such as pinacol or the like), $R_{50}$ represents O or S;

$R_{51}$ represents $N_3$, $SH_2$, $NH_2$, $NO_2$ or $OR'_7$;

$R_{52}$ represents hydrogen, a lower alkyl, an amine, $OR'_7$, or a pharmaceutically acceptable salt, or $R_{51}$ and $R_{52}$ taken together with the phosphorous atom to which they are attached complete a heterocyclic ring having from 5 to 8 atoms in the ring structure $X_1$ represents a halogen;

$X_2$ and $X_3$ each represent a hydrogen or a halogen m is zero or an integer in the range of 1 to 8; and n is an integer in the range of 1 to 8.

In preferred embodiments, $R_1$ is

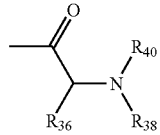

wherein $R_{36}$ is a small hydrophobic group, e.g., a lower alkyl or a halogen and $R_{38}$ is hydrogen, or, $R_{36}$ and $R_{37}$ together form a 4-7 membered heterocycle including the N and the Cα carbon, as defined for A above; and $R_{40}$ represents a C-terminally linked amino acid residue or amino acid analog, or a C-terminally linked peptide or peptide analog, or an amino-protecting group.

In preferred embodiments, $R_3$ is a hydrogen, or a small hydrophobic group such as a lower alkyl or a halogen.

In preferred embodiments, $R_5$ is a hydrogen, or a halogentated lower alkyl.

In preferred embodiments, $X_1$ is a fluorine, and $X_2$ and $X_3$, if halogens, are fluorine.

In preferred embodiments, $R_{61}$ and $R_{62}$, independently, represent low alkyls, such as methyl, ethyl, propyl, isopropyl, tert-butyl or the like.

Also included are such peptidomimetics as olefins, phosphonates, aza-amino acid analogs and the like.

Another representative class of compounds for use in the method of the present invention are represented by the general formula (as described in U.S. provisional application entitled "Methods for Regulating Glucose Metabolism, and Reagents Related Thereto" filed on Nov. 26, 2001, which is incorporated herein by reference):

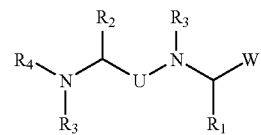

wherein, $R_1$ represents hydrogen, halogen or lower alkyl, lower alkenyl, or lower alkynyl, preferably lower alkyl such as methyl, ethyl, etc., optionally substituted by one or more small substitutents such as halogen, hydroxy, alkoxy, etc.;

$R_2$ represents a branched lower alkyl, aralkyl, aryl, heteroaralkyl, heteroaryl, cycloalkyl, or cycloalkylalkyl, preferably a bulky hydrophobic group, such as cyclohexyl, t-butyl, etc., optionally substituted by one or more small substitutents such as halogen, hydroxy, alkoxy, etc.;

$R_3$ represents hydrogen or an amino-protecting group, preferably hydrogen;

$R_4$ represents hydrogen, a C-terminally linked amino acid residue or amino acid analog, a C-terminally linked peptide or peptide analog, an amino-protecting group, or

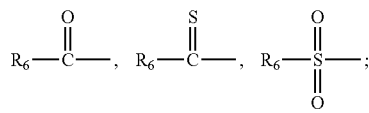

$R_6$ represents hydrogen, a halogen, a alkyl, an alkenyl, an alkynyl, an aryl, —($CH_2$)$_m$—$R_7$, —($CH_2$)$_m$—OH, —($CH_2$)$_m$—O-alkyl, —($CH_2$)$_m$—O-alkenyl, —($CH_2$)$_m$—O-alkynyl, —($CH_2$)$_m$—O—($CH_2$)$_m$—$R_7$, —($CH_2$)$_m$—SH, —($CH_2$)$_m$—S-alkyl, —($CH_2$)$_m$—S-alkenyl, —($CH_2$)$_m$—S-alkynyl, —($CH_2$)$_m$—S—($CH_2$)$_m$—$R_7$;

$R_7$ represents, for each occurrence, a substituted or unsubstituted aryl, aralkyl, cycloalkyl, cycloalkenyl, or heterocycle;

$R'_7$ represents, for each occurrence, hydrogen, or a substituted or unsubstituted alkyl, alkenyl, aryl, aralkyl, cycloalkyl, cycloalkenyl, or heterocycle;

U is absent or represents —C(=O)—, —C(=S)—, —P(=O)(O$R_8$)—, —S($O_2$)—, or —S(O)—, preferably —C(=O)—, —C(=S)—, or —S($O_2$)—;

W represents a functional group which reacts with an active site residue of the targeted protease, as for example, —CN, —CH=N$R_{53}$,

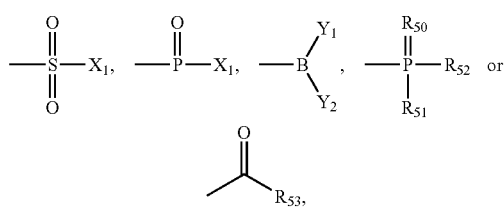

preferably

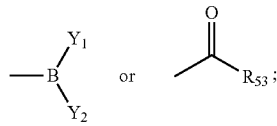

$Y_1$ and $Y_2$ are, independently, OH, or a group capable of being hydrolyzed, e.g., under physiologic conditions to a hydroxyl group, such as alkoxy, aryloxy, etc., including cyclic derivatives where $Y_1$ and $Y_2$ are connected via a ring having from 5 to 8 atoms in the ring structure (such as pinacol or the like);

$R_{50}$ represents O or S;

$R_{51}$ represents $N_3$, SH, $NH_2$, $NO_2$ or $OR'_7$;

$R_{52}$ represents hydrogen, a lower alkyl, an amine, $OR'_7$, or a pharmaceutically acceptable salt, or $R_{51}$ and $R_{52}$ taken together with the phosphorous atom to which they are attached complete a heterocyclic ring having from 5 to 8 atoms in the ring structure;

$R_{53}$ represents hydrogen, an alkyl, an alkenyl, an alkynyl, —$C(X_1)(X_2)$—$X_3$, —$(CH_2)_m$—$R_7$, —$(CH_2)_n$—OH, —$(CH_2)_n$—O-alkyl, —$(CH_2)_n$—O-alkenyl, —$(CH_2)_n$—O-alkynyl, —$(CH_2)_n$—O—$(CH_2)_m$—$R_7$, —$(CH_2)_n$—SH, —$(CH_2)_n$—S-alkyl, —$(CH_2)_n$—S-alkenyl, —$(CH_2)_n$—S-alkynyl, —$(CH_2)_n$—S—$(CH_2)_m$—$R_7$, —$C(O)C(O)NH_2$, —$C(O)C(O)OR'_7$;

$X_1$ represents a halogen, preferably a fluorine;

$X_2$ and $X_3$ each represent a hydrogen or a halogen, preferably a hydrogen or a fluorine;

m is zero or an integer in the range of 1 to 8;

and n is an integer in the range of 1 to 8.

In preferred embodiments, the subject method utilizes, as a DPIV inhibitor, a boronic acid analog of an amino acid. For example, the present invention contemplates the use of boroalanine derivatives in the subject method. Exemplary boronic acid derived inhibitors of the present invention are represented by the general formula:

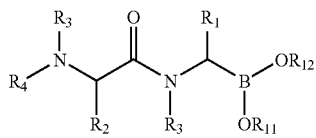

wherein $R_1$ represents hydrogen, halogen or lower alkyl, lower alkenyl, or lower alkynyl, preferably lower allyl such as methyl, ethyl, etc., optionally substituted by one or more small substitutents such as halogen, hydroxy, alkoxy, etc.;

$R_2$ represents a branched lower alkyl, aralkyl, aryl, heteroaralkyl, heteroaryl, cycloalkyl, or cycloalkylalkyl, preferably a bulky hydrophobic group, such as cyclohexyl, t-butyl, etc., optionally substituted by one or more small substitutents such as halogen, hydroxy, alkoxy, etc.;

$R_3$ represents hydrogen or an amino-protecting group, preferably hydrogen;

$R_4$ represents hydrogen, a C-terminally linked amino acid residue or amino acid analog, a C-terminally linked peptide or peptide analog, an amino-protecting group, or

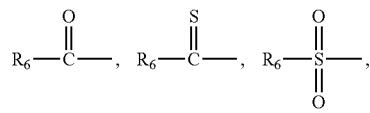

preferably hydrogen.

$R_6$ represents hydrogen, a halogen, a alkyl, an alkenyl, an alkynyl, an aryl, —$(CH_2)_m$—$R_7$, —$(CH_2)_m$—OH, —$(CH_2)_m$—O-alkyl, —$(CH_2)_m$—O-alkenyl, —$(CH_2)_m$—O-alkynyl, —$(CH_2)_m$—O—$(CH_2)_m$—$R_7$, —$(CH_2)_m$—SH, —$(CH_2)_m$—S-alkyl, —$(CH_2)_m$—S-alkenyl, —$(CH_2)_m$—S-alkynyl, —$(CH_2)_m$—S—$(CH_2)_m$—$R_7$;

$R_7$ represents, for each occurrence, a substituted or unsubstituted aryl, aralkyl, cycloalkyl, cycloalkenyl, or heterocycle;

$R_{11}$ and $R_{12}$ each independently represent hydrogen, an alkyl, or a pharmaceutically acceptable salt, or $R_{11}$ and $R_{12}$ taken together with the O—B—O atoms to which they are attached complete a heterocyclic ring having from 5 to 8 atoms in the ring structure; and m is zero or an integer in the range of 1 to 8.

In other embodiments, the subject DPIV inhibitors include aldehyde analogs of alanine or alanyl derivatives. Exemplary aldehyde-derived inhibitors of the present invention are represented by the general formula:

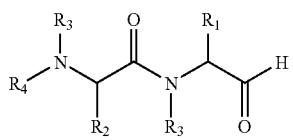

wherein $R_1$ represents hydrogen, halogen or lower alkyl, lower alkenyl, or lower alkynyl, preferably lower alkyl such as methyl, ethyl, etc., optionally substituted by one or more small substitutents such as halogen, hydroxy, alkoxy, etc.;

$R_2$ represents a branched lower alkyl, aralkyl, aryl, heteroaralkyl, heteroaryl, cycloalkyl, or cycloalkylalkyl, preferably a bulky hydrophobic group, such as cyclohexyl, t-butyl, etc., optionally substituted by one or more small substitutents such as halogen, hydroxy, alkoxy, etc.;

$R_3$ represents hydrogen or an amino-protecting group, preferably hydrogen;

$R_4$ represents hydrogen, a C-terminally linked amino acid residue or amino acid analog, a C-terminally linked peptide or peptide analog, an amino-protecting group, or

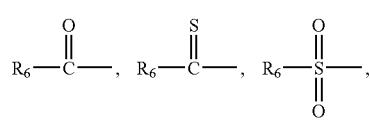

preferably hydrogen.

$R_6$ represents hydrogen, a halogen, a alkyl, an alkenyl, an alkynyl, an aryl, —$(CH_2)_m$—$R_7$, —$(CH_2)_m$—OH, —$(CH_2)_m$—O-alkyl, —$(CH_2)_m$—O-alkenyl, —$(CH_2)_m$—O-alkynyl, —$(CH_2)_m$—O—$(CH_2)_m$—$R_7$, —$(CH_2)_m$—SH, —$(CH_2)_m$—S-alkyl, —$(CH_2)_m$—S-alkenyl, —$(CH_2)_m$—S-alkynyl, —$(CH_2)_m$—S—$(CH_2)_m$—$R_7$;

$R_7$ represents, for each occurrence, a substituted or unsubstituted aryl, aralkyl, cycloalkyl, cycloalkenyl, or heterocycle;

m is zero or an integer in the range of 1 to 8.

In yet further embodiments, the subject DPIV inhibitors are halo-methyl ketone analogs of an amino acid. Exemplary inhibitors of this class include compounds represented by the general formula:

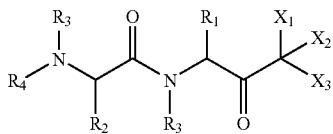

wherein, $R_1$ represents hydrogen, halogen or lower alkyl, lower alkenyl, or lower alkynyl, preferably lower alkyl such as methyl, ethyl, etc., optionally substituted by one or more small substitutents such as halogen, hydroxy, alkoxy, etc.;

$R_2$ represents a branched lower alkyl, aralkyl, aryl, heteroaralkyl, heteroaryl, cycloalkyl, or cycloalkylalkyl, preferably a bulky hydrophobic group, such as cyclohexyl, t-butyl, etc., optionally substituted by one or more small substitutents such as halogen, hydroxy, alkoxy, etc.;

$R_3$ represents hydrogen or an amino-protecting group, preferably hydrogen;

$R_4$ represents hydrogen, a C-terminally linked amino acid residue or amino acid analog, a C-terminally linked peptide or peptide analog, an amino-protecting group, or

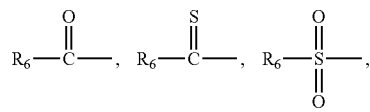

preferably hydrogen.

$R_6$ represents hydrogen, a halogen, a alkyl, an alkenyl, an alkynyl, an aryl, —$(CH_2)$—$R_7$, —$(CH_2)_m$—OH, —$(CH_2)_m$—O-alkyl, —$(CH_2)_m$—O-alkenyl, —$(CH_2)_m$—O-alkynyl, —$(CH_2)_m$—O—$(CH_2)_m$—$R_7$, —$(CH_2)_m$—SH, —$(CH_2)_m$—S-alkyl, —$(CH_2)_m$—S-alkenyl, —$(CH_2)_m$—S-alkynyl, —$(CH_2)_m$—S—$(CH_2)_m$—$R_7$;

$R_7$ represents, for each occurrence, a substituted or unsubstituted aryl, aralkyl, cycloalkyl, cycloalkenyl, or heterocycle;

$X_1$, $X_2$ and $X_3$ each represent a hydrogen or a halogen;

m is zero or an integer in the range of 1 to 8.

In preferred embodiments, the DPIV inhibitor is a peptide or peptidomimetic including a alaninyl group or analog thereof in the P1 specificity position, and a non-naturally occurring amino acid in the P2 specificity position, or an analog thereof. For example, the DPIV inhibitor may include an Cyclohexylglycine-Ala or t-butylglycine-Ala dipeptide sequence or equivalent thereof, and be represented in the general formula:

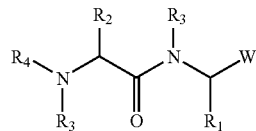

$R_1$ represents hydrogen, halogen or lower alkyl, lower alkenyl, or lower alkynyl, preferably lower alkyl such as methyl, ethyl, etc., optionally substituted by one or more small substitutents such as halogen, hydroxy, alkoxy, etc.;

$R_2$ represents a branched lower alkyl, aralkyl, aryl, heteroaralkyl, heteroaryl, cycloalkyl, or cycloalkylalkyl, preferably a bulky hydrophobic group, such as cyclohexyl, t-butyl, etc., optionally substituted by one or more small substitutents such as halogen, hydroxy, alkoxy, etc.;

$R_3$ represents hydrogen or an amino-protecting group, preferably hydrogen;

$R_4$ represents hydrogen, a C-terminally linked amino acid residue or amino acid analog, a C-terminally linked peptide or peptide analog, an amino-protecting group, or

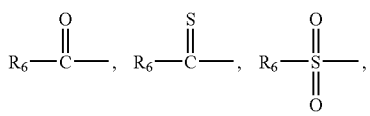

preferably hydrogen.

$R_6$ represents hydrogen, a halogen, a alkyl, an alkenyl, an alkynyl, an aryl, —$(CH_2)_m$—$R_7$, —$(CH_2)_m$—OH, —$(CH_2)_m$—O-alkyl, —$(CH_2)_m$—O-alkenyl, —$(CH_2)_m$—O-alkynyl, —$(CH_2)_m$—O—$(CH_2)_m$—$R_7$, —$(CH_2)_m$—SH, —$(CH_2)_m$—S-alkyl, —$(CH_2)_m$—S-alkenyl, —$(CH_2)_n$, —S-alkynyl, —$(CH_2)_m$—S—$(CH_2)_m$—$R_7$;

$R_7$ represents, for each occurrence, a substituted or unsubstituted aryl, aralkyl, cycloalkyl, cycloalkenyl, or heterocycle; W represents a functional group which reacts with an active site residue of the targeted protease, as for example, —CN, —CH=$NR_{53}$,

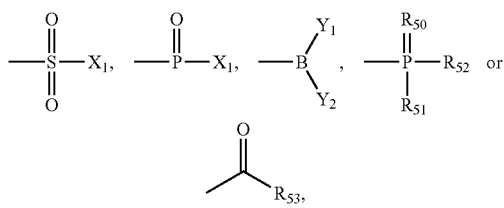

preferably

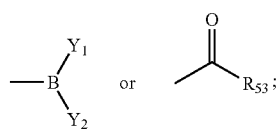

$Y_1$ and $Y_2$ are, independently, OH, or a group capable of being hydrolyzed, e.g., under physiologic conditions to a hydroxyl group, such as alkoxy, aryloxy, etc., including cyclic derivatives where $Y_1$ and $Y_2$ are connected via a ring having from 5 to 8 atoms in the ring structure (such as pinacol or the like);

$R_{50}$ represents O or S;

$R_{51}$ represents $N_3$, SH, $NH_2$, $NO_2$ or $OR'_7$;

$R_{52}$ represents hydrogen, a lower alkyl, an amine, $OR'_7$, or a pharmaceutically acceptable salt, or $R_{51}$ and $R_{52}$ taken together with the phosphorous atom to which they are attached complete a heterocyclic ring having from 5 to 8 atoms in the ring structure;

$R_{53}$ represents hydrogen, an alkyl, an alkenyl, an alkynyl, $-C(X_1)(X_2)-X_3$, $-(CH_2)_m-R_7$, $-(CH_2)_n-OH$, $-(CH_2)_n-O$-alkyl, $-(CH_2)_n-O$-alkenyl, $-(CH_2)_n-O$-alkynyl, $-(CH_2)_n-O-(CH_2)_m-R_7$, $-(CH_2)_n-SH$, $-(CH_2)_n-S$-alkyl, $-(CH_2)_n-S$-alkenyl, $-(CH_2)_n-S$-alkynyl, $-(CH_2)_n-S-(CH_2)_m-R_7$, $-C(O)C(O)NH_2$, $-C(O)C(O)OR'_7$, preferably a hydrogen, or a halogentated lower alkyl;

$X_1$ represents a halogen, preferably a fluorine;

m is zero or an integer in the range of 1 to 8; and n is an integer in the range of 1 to 8.

Another representative class of compounds for use in the subject method include peptide and peptidomimetics of (L)-Ala-(L)-Cyclohexylglycine, e.g., preserving the steric disposition of moieties. Such inhibitors include compounds represented by the general formula:

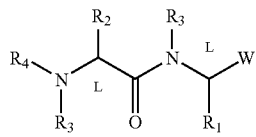

wherein, $R_1$ represents hydrogen, halogen or lower alkyl, lower alkenyl, or lower alkynyl, preferably lower alkyl such as methyl, ethyl, etc., optionally substituted by one or more small substitutents such as halogen, hydroxy, alkoxy, etc.;

$R_2$ represents a branched lower alkyl, aralkyl, aryl, heteroaralkyl, heteroaryl, cycloalkyl, or cycloalkylalkyl, preferably a bulky hydrophobic group, such as cyclohexyl, t-butyl, etc., optionally substituted by one or more small substituents such as halogen, hydroxy, alkoxy, etc.;

$R_3$ represents hydrogen or an amino-protecting group, preferably hydrogen;

$R_4$ represents hydrogen, a C-terminally linked amino acid residue or amino acid analog, a C-terminally linked peptide or peptide analog, an amino-protecting group, or

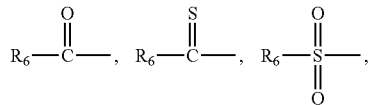

preferably hydrogen.

$R_6$ represents hydrogen, a halogen, a alkyl, an alkenyl, an alkynyl, an aryl, $-(CH_2)_m-R_7$, $-(CH_2)_m-OH$, $-(CH_2)_m-O$-alkyl, $-(CH_2)_m-O$-alkenyl, $-(CH_2)_m-O$-alkynyl, $-(CH_2)_m-O-(CH_2)_m-R_7$, $-(CH_2)_m-SH$, $-(CH_2)_m-S$-alkyl, $-(CH_2)_m-S$-alkenyl, $-(CH_2)_m-S$-alkynyl, $-(CH_2)_m-S-(CH_2)_m-R_7$;

$R_7$ represents, for each occurrence, a substituted or unsubstituted aryl, aralkyl, cycloalkyl, cycloalkenyl, or heterocycle;

W represents a functional group which reacts with an active site residue of the targeted protease, as for example, $-CN$, $-CH=NR_{53}$,

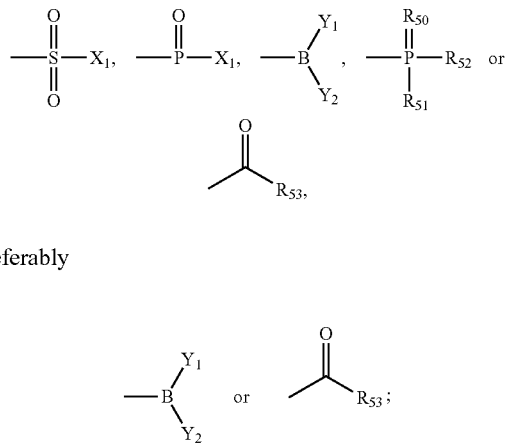

preferably $Y_1$ and $Y_2$ are, independently, OH, or a group capable of being hydrolyzed, e.g., under physiologic conditions to a hydroxyl group, such as alkoxy, aryloxy, etc., including cyclic derivatives where $Y_1$ and $Y_2$ are connected via a ring having from 5 to 8 atoms in the ring structure (such as pinacol or the like);

$R_{50}$ represents O or S;

$R_{51}$ represents $N_3$, SH, $NH_2$, $NO_2$ or $OR'_7$;

$R_{52}$ represents hydrogen, a lower alkyl, an amine, $OR'_7$, or a pharmaceutically acceptable salt, or $R_{51}$ and $R_{52}$ taken together with the phosphorous atom to which they are attached complete a heterocyclic ring having from 5 to 8 atoms in the ring structure;

$R_{53}$ represents hydrogen, an alkyl, an alkenyl, an alkynyl, $-C(X_1)(X_2)-X_3$, $-(CH_2)_m-R_7$, $-(CH_2)_n-OH$, $-(CH_2)_n-O$-alkyl, $-(CH_2)_n-O$-alkenyl, $-(CH_2)_n-O$-alkynyl, $-(CH_2)_n-O-(CH_2)_m-R_7$, $-(CH_2)_n-SH$, $-(CH_2)_n-S$-alkyl, $-(CH_2)_n-S$-alkenyl, $-(CH_2)_n-S$-alkynyl, $-(CH_2)_n-S-(CH_2)_m-R_7$, $-C(O)C(O)NH_2$, $-C(O)C(O)OR'_7$, preferably a hydrogen, or a halogentated lower alkyl;

$X_1$ represents a halogen, preferably a fluorine;

m is zero or an integer in the range of 1 to 8;

and n is an integer in the range of 1 to 8.

Also deemed as equivalents are any compounds which can be hydrolytically converted into any of the aforementioned compounds including boronic acid esters and halides, and carbonyl equivalents including acetals, hemiacetals, ketals, and hemiketals, and cyclic dipeptide analogs.

As used herein, the definition of each expression, e.g. alkyl, m, n, etc., when it occurs more than once in any structure, is intended to be independent of its definition elsewhere in the same structure.

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

The pharmaceutically acceptable salts of the present invention can be synthesized from the subject compound which contain a basic or acid moiety by conventional chemical methods. Generally, the salts are prepared by reacting the free base or acid with stoichiometric amounts or with an excess of the desired salt-forming inorganic or organic acid or base in a suitable solvent. The pharmaceutically acceptable salts of the acids of the subject compounds are also readily prepared by conventional procedures such as treating an acid with an appropriate amount of a base such as an alkali or alkaline earth methyl hydroxide (e.g. sodium, potassium, lithium, calcium or magnesium) or an organic base such as an amine, piperidine, pyrrolidine, benzylamine and the like, or a quaternary ammonium hydroxide such as tetramethylammonium hydroxide and the like.

Contemplated equivalents of the compounds described above include compounds which otherwise correspond thereto, and which have the same general properties thereof (e.g. the ability to inhibit proteolysis of GLP-1 or other peptide hormone or precursor thereof), wherein one or more simple variations of substituents are made which do not adversely affect the efficacy of the compound in use in the contemplated method. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

In other embodiments of the methods, the present invention further contemplates the use of known DPIV inhibitors in the art, such as, for example, TMC-2A, TMC-2B and TMC-2C (Nonaka (1997) J. Antibiot (Tokyo) 50(8):646-652); Lys[Z(NO$_2$)]-thiazolidide, Lys[Z(NO$_2$)]-piperidide, and Lys[Z(NO$_2$)]-pyrrolidide (Reinhold et al. (1997) Immunology 91(3):354-360); Phenylalanyl-pyrrolidine-2-nitrile and arginyl(PMC)-pyrrolidine-2-nitrile (Jiang et al (1997) Res. Virol. 148(4):255-266); Ala-Pro-nitrobenzoylhydroxylamine (Tanaka et al (1997) Int J Immunopharmacol 19(1):15-24; Ala-PipP(OPh-4-Cl)$_2$, Ala-ProP(OPh)$_2$, Ala-ProP(OPh-4-Cl)$_2$, (Boduszek et al (1994) J Med Chem 37(23):3969-3976; diprotin A and diprotin B (Umezawa et al (1984) J Antibiotics 37:422-425); 4-amino-(2,6-dimethylphenyl)phthalimides, 4- and 5-hydroxy-(2,6-diethylphenyl)phthalimide, and 4-hydroxy-(2,6-diisopropylphenyl)phthalimide (Shimazawa et al (1999) Bioorg Med Chem Lett 9(4):559-562). Latest developments in the search of DPIV inhibitors have also been reviewed (Augustyns et al (1999) Curr Med Chem 6(4):311-327). All of the above-cited references and publications are hereby incorporated by reference.

ii. Definitions

For convenience, before further description of the present invention, certain terms employed in the specification, examples, and appended claims are collected here.

The term "alkyl" refers to the radical of saturated aliphatic groups, including straight-chain alkyl groups, branched-chain alkyl groups, cycloalkyl(alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Likewise, preferred cycloalkyls have from 3-carbon atoms in their ring structure, and more preferably have 5, 6 or 7 carbons in the ring structure.

Moreover, the term "alkyl" (or "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an ester, a formyl, or a ketone), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN and the like. Exemplary substituted alkyls are described below. Cycloalkyls can be further substituted with alkyls, alkenyls, alkoxys, alkylthios, aminoalkyls, carbonyl-substituted alkyls, —CF$_3$, —CN, and the like.

The term "aralkyl", as used herein, refers to an allyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

The term "heteroatom" as used herein means an atom of any element other than carbon or hydrogen. Preferred heteroatoms are nitrogen, oxygen, sulfur and phosphorous.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art recognized and refer to both unsubstituted and substituted amines, e.g., a moiety that can be represented by the general formula:

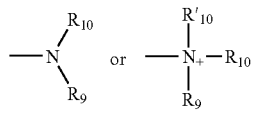

wherein $R_9$, $R_{10}$ and $R'_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e., at least one of $R_9$ and $R_{10}$ is an alkyl group.

The term "acylamino" is art-recognized and refers to a moiety that can be represented by the general formula:

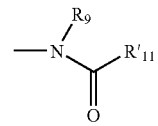

wherein R9 is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

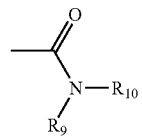

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

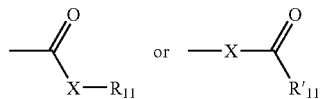

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R_{11}$ is hydrogen, the formula represents a "thioformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

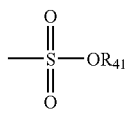

in which $R_{41}$ is an electron pair, hydrogen, alkyl, cycloalkyl, or aryl.

The term "sulfate" is art recognized and includes a moiety that can be represented by the general formula:

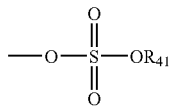

in which $R_{41}$ is as defined above.

The term "sulfonamido" is art recognized and includes a moiety that can be represented by the general formula:

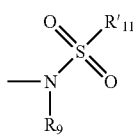

in which $R_9$ and $R'_{11}$ are as defined above.

The term "sulfamoyl" is art-recognized and includes a moiety that can be represented by the general formula:

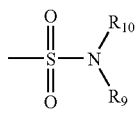

in which $R_9$ and $R_{10}$ are as defined above.

The terms "sulfoxido" or "sulfinyl", as used herein, refers to a moiety that can be represented by the general formula:

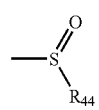

in which $R_{44}$ is selected from the group consisting of hydrogen, alkyl, alkenyl, alkynyl, cycloalkyl, heterocyclyl, aralkyl, or aryl.

A "phosphoryl" can in general be represented by the formula:

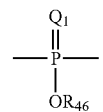

wherein $Q_1$ represented S or O, and $R_{46}$ represents hydrogen, a lower alkyl or an aryl. When used to substitute, e.g., an alkyl, the phosphoryl group of the phosphorylalkyl can be represented by the general formula:

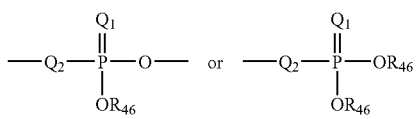

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphorothioate".

A "phosphoramidite" can be represented in the general formula:

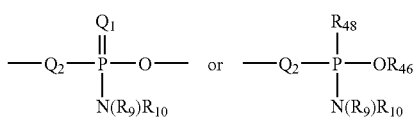

wherein $R_9$ and $R_{10}$ are as defined above, and $Q_2$ represents O, S or N.

A "phosphonamidite" can be represented in the general formula:

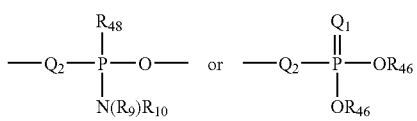

wherein $R_9$ and $R_{10}$ are as defined above, $Q_2$ represents O, S or N, and $R_{48}$ represents a lower alkyl or an aryl, $Q_2$ represents O, S or N.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

A "small" substituent is one of 10 atoms or less.

By the terms "amino acid residue" and "peptide residue" is meant an amino acid or peptide molecule without the —OH of its carboxyl group. In general the abbreviations used herein for designating the amino acids and the protective groups are based on recommendations of the IUPAC-IUB Commission on Biochemical Nomenclature (see Biochemistry (1972) 11:1726-1732). For instance Met, Ile, Leu, Ala and Gly represent "residues" of methionine, isoleucine, leucine, alanine and glycine, respectively. By the residue is meant a radical derived from the corresponding α-amino acid by eliminating the OH portion of the carboxyl group and the H portion of the α-amino group. The term "amino acid side chain" is that part of an amino acid exclusive of the —CH(NH$_2$)COOH portion, as defined by K. D. Kopple, "Peptides and Amino Acids", W. A. Benjamin Inc., New York and Amsterdam, 1966, pages 2 and 33; examples of such side chains of the common amino acids are —CH$_2$CH$_2$SCH$_3$ (the side chain of methionine), —CH$_2$(CH$_3$)—CH$_2$CH$_3$ (the side chain of isoleucine), —CH$_2$CH(CH$_3$)$_2$ (the side chain of leucine) or H-(the side chain of glycine).

For the most part, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan, and those amino acids and amino acid analogs which have been identified as constituents of peptidylglycan bacterial cell walls.

The term amino acid residue further includes analogs, derivatives and congeners of any specific amino acid referred to herein, as well as C-terminal or N-terminal protected amino acid derivatives (e.g. modified with an N-terminal or C-terminal protecting group). For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups). For instance, the subject compound can include an amino acid analog such as, for example, cyanoalanine, canavanine, djenkolic acid, norleucine, 3-phosphoserine, homoserine, dihydroxy-phenylalanine, 5-hydroxytryptophan, 1-methylhistidine, 3-methylhistidine, diaminopimelic acid, ornithine, or diaminobutyric acid. Other naturally occurring amino acid metabolites or precursors having side chains which are suitable herein will be recognized by those skilled in the art and are included in the scope of the present invention.

Also included are the (D) and (L) stereoisomers of such amino acids when the structure of the amino acid admits of stereoisomeric forms. The configuration of the amino acids and amino acid residues herein are designated by the appropriate symbols (D), (L) or (DL), furthermore when the configuration is not designated the amino acid or residue can have the configuration (D), (L) or (DL). It will be noted that the structure of some of the compounds of this invention includes asymmetric carbon atoms. It is to be understood accordingly that the isomers arising from such asymmetry are included within the scope of this invention. Such isomers can be obtained in substantially pure form by classical separation techniques and by sterically controlled synthesis. For the purposes of this application, unless expressly noted to the contrary, a named amino acid shall be construed to include both the (D) or (L) stereoisomers.

The phrase "protecting group" as used herein means substituents which protect the reactive functional group from undesirable chemical reactions. Examples of such protecting groups include esters of carboxylic acids and boronic acids, ethers of alcohols and acetals and ketals of aldehydes and ketones. For instance, the phrase "N-terminal protecting group" or "amino-protecting group" as used herein refers to various amino-protecting groups which can be employed to protect the N-terminus of an amino acid or peptide against undesirable reactions during synthetic procedures. Examples of suitable groups include acyl protecting groups such as, to illustrate, formyl, dansyl, acetyl, benzoyl, trifluoroacetyl, succinyl and methoxysuccinyl; aromatic urethane protecting groups as, for example, benzyloxycarbonyl (Cbz); and aliphatic urethane protecting groups such as t-butoxycarbonyl (Boc) or 9-Fluorenylmethoxycarbonyl (FMOC).

As noted above, certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and non-aromatic organic compounds which can be substituted or unsubstituted.

A compound is said to have an "insulinotropic activity" if it is able to stimulate, or cause the stimulation of, the synthesis or expression of the hormone insulin.

The phrase "targeted by" refers to cells which are attacked and/or gradually destroyed by an autoimmune disease. For example, in Type I diabetes white blood cells called T lymphocytes produce immune factors called cytokines that attack and gradually destroy the beta cells of the pancreas.

iii. Exemplary Formulations

The inhibitors useful in the subject methods possess, in certain embodiments, the ability to lower blood glucose levels, to relieve obesity, to alleviate impaired glucose tolerance, to inhibit hepatic glucose neogenesis, to inhibit diabetic ketoacidosis, and to lower blood lipid levels and to inhibit aldose reductase. They are thus useful for the prevention and/or therapy of hyperglycemia, obesity, hyperlipidemia, diabetic complications (including retinopathy, nephropathy, neuropathy, cataracts, coronary artery disease and arteriosclerosis) and furthermore for obesity-related hypertension and osteoporosis.

Diabetes mellitus is a disease characterized by hyperglycemia occurring from a relative or absolute decrease in insulin secretion, decreased insulin sensitivity or insulin resistance. The morbidity and mortality of this disease result from vascular, renal, and neurological complications. An oral glucose tolerance test is a clinical test used to diagnose diabetes. In an oral glucose tolerance test, a patient's physiological response to a glucose load or challenge is evaluated. After ingesting the glucose, the patient's physiological response to the glucose challenge is evaluated. Generally, this is accomplished by determining the patient's blood glucose levels (the concentration of glucose in the patient's plasma, serum or whole blood) for several predetermined points in time.

As described in the appended examples, we demonstrate that, in vivo, high affinity inhibitors of DPIV are biologically active with respect to regulation of glucose metabolism. For example, a single injection of the inhibitor Pro-boro-Pro (see examples for structure) was alone sufficient to improve glucose control. A single injection of Pro-boro-Pro was also observed to potentiate the response to a subtherapeutic dose of GLP-1. We have also observed that chronic (>5 days) treatment with Pro-boro-Pro alone lowers both fasting blood sugars, and the glycemic excursion to oral glucose challenge.

As indicated above, the inhibitors useful in the subject method can be peptide- or peptidomimetic-derived inhibitors of the target proteolytic activity, or can be a non-peptide compound identified, e.g., by drug screening assays described herein.

As discussed further below, a variety of assays are available in the art for identifying potential inhibitors of DPIV and the like, as well as assessing the various biological activities (including side-effects and toxicity) of such an inhibitor.

A. Examples of Peptidyl DPIV Inhibitors

In the case of DPIV inhibitors, a preferred class of inhibitors are peptidyl compounds based on the dipeptides Pro-Pro or Ala-Pro. Another preferred class of peptidyl inhibitors are compounds based on the dipeptide (D)-Ala-(L)-Ala. In many embodiments, it will be desirable to provide the peptidyl moiety as a peptidomimetic, e.g., to increase bioavailability and/or increase the serum half-life relative to the equivalent peptide. For instance, a variety of peptide backbone analogs are available in the art and be readily adpated for use in the subject methods.

In an exemplary embodiment, the peptidomimetic can be derived as a retro-inverso analog of the peptide. To illustrate, certain of the subject peptides can be generated as the retro-inverso analog (shown in its unprotected state):

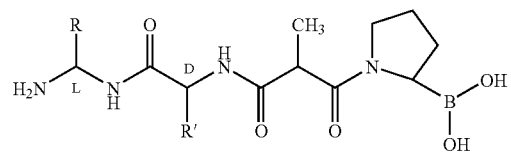

Such retro-inverso analogs can be made according to the methods known in the art, such as that described by the Sisto et al. U.S. Pat. No. 4,522,752. For example, the illustrated retro-inverso analog can be generated as follows. The geminal diamine corresponding to the N-terminal amino acid analogs is synthesized by treating an N-Boc-protected amino acid (having the sidechain R) with ammonia under HOBT-DCC coupling conditions to yield amide, and then effecting a Hofmann-type rearrangement with I,I-bis-(trifluoroacetoxy) iodobenzene (TIB), as described in Radhakrishna et al. (1979) J. Org. Chem. 44:1746. The product amine salt is then coupled to a side-chain protected (e.g., as the benzyl ester) N-Fmoc D-enatiomer of the second amino acid residue (e.g., having a sidechain R') under standard conditions to yield the pseudodipeptide. The Fmoc (fluorenylmethoxycarbonyl) group is removed with piperidine in dimethylformamide, and the resulting amine is trimethylsilylated with bistrimethylsilylacetamide (BSA) before condensation with suitably alkylated, side-chain protected derivative of Meldrum's acid, as described in U.S. Pat. No. 5,061,811 to Pinori et al., to yield the retro-inverso tripeptide analog. The pseudotripeptide is then coupled with (protected) boro-proline under standard conditions to give the protected tetrapeptide analog. The protecting groups are removed to release the final product, which is purified by HPLC.

In another illustrative embodiment, the peptidomimetic can be derived as a retro-enantio analog of the peptide:

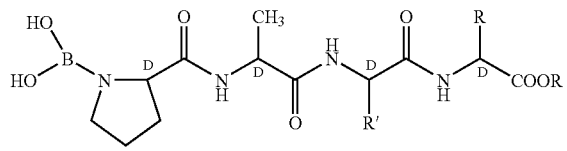

Retro-enantio analogs such as this can be synthesized using D-enatiomers of commercially available D-amino acids or other amino acid analogs and standard solid- or solution-phase peptide-synthesis techniques.

In still another illustrative embodiment, trans-olefin derivatives can be made with the subject boronophenylalanine analogs. For example, an exemplary olefin analog is:

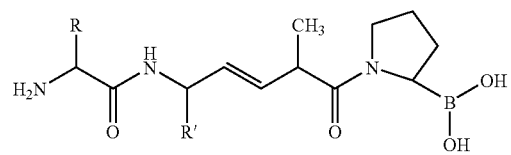

The trans olefin analog can be synthesized according to the method of Y. K. Shue et al. (1987) Tetrahedron Letters 28:3225.

Still another class of peptidomimetic boronophenylalanine derivatives include the phosphonate derivatives, such as:

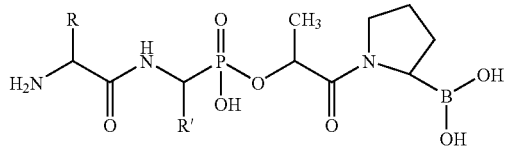

The synthesis of such phosphonate derivatives can be adapted from known synthesis schemes. See, for example, Loots et al. in *Peptides: Chemistry and Biology*, (Escom Science Publishers, Leiden, 1988, p. 118); Petrillo et al. in *Peptides: Structure and Function* (Proceedings of the 9th American Peptide Symposium, Pierce Chemical Co. Rockland, Ill., 1985).

B. Non-Peptidyl DPIV Inhibitors

The pharmaceutical industry has developed a variety of different strategies for assessing millions of compounds a year as potential lead compounds based on inhibitory activity against an enzyme. DPIV and other proteolytic enzymes targeted by the subject method are amenable to the types of high throughput screening required to sample large arrays of compounds and natural extracts for suitable inhibitors.

As an illustrative embodiment, the ability of a test agent to inhibit DPIV can be assessed using a colorimetric or fluorometric substrate, such as Ala-Pro-paranitroanilide. See U.S. Pat. No. 5,462,928. Moreover, DPIV can be purified, and is accordingly readily amenable for use in such high throughput formats as multi-well plates.

Briefly, DPIV is purified from pig kidney cortex (Barth et al. (1974) *Acta Biol Med Germ* 32:157; Wolf et al. (1972) *Acta Bio Mes Germ* 37:409) or human placenta (Puschel et al. (1982) *Eur J Biochem* 126:359). An illustrative reaction mixture includes 50 µM sodium Hepes (pH7.8), 10 µM Ala-Pro-paranitroanilide, 6 milliunits of DPIV, and 2% (v/v) dimethylformamide in a total volume of 1.0 mL. The reaction is initiated by addition of enzyme, and formation of reaction product (paranitroanilide) in the presence and absence of a test compound can be detected photometrically, e.g., at 410 nm.

Exemplary compounds which can be screened for activity against DPIV (or other relevant enzymes) include peptides, nucleic acids, carbohydrates, small organic molecules, and natural product extract libraries, such as isolated from animals, plants, fungus and/or microbes.

C. Assays of Insulinotropic Activity

In selecting a compound suitable for use in the subject method, it is noted that the insulinotropic property of a compound may be determined by providing that compound to animal cells, or injecting that compound into animals and monitoring the release of immunoreactive insulin (IRI) into the media or circulatory system of the animal, respectively. The presence of IRI can be detected through the use of a radioimmunoassay which can specifically detect insulin.

Nonobese diabetic (NOD) mice are a well established model of type I diabetes (IDDM). In most litters, a prediabetic (>20 weeks) phase is observed which is characterized by pancreatic insulitis without hyperglycemia. The NOD mice can purchased from, for example, The Jackson Laboratories (Bar Harbor, Me.). In an exemplary embodiment, for treatment of the mice with a regimen including a DPIV inhibitor or control, sub-orbital sinus blood samples are taken before and at some time (e.g., 60 minutes) after dosing of each animal. Blood glucose measurements can be made by any of several conventional techniques, such as using a glucose meter. The blood glucose levels of the control and DPIV inhibitor dosed animals are compared.

The metabolic fate of exogenous GLP-1 can also be followed in either nondiabetic and type I diabetic subjects, and the effect of a candidate DPIV inhibitor determined. For instance, a combination of high-pressure liquid chromatography (HPLC), specific radioimmunoassays (RIAs), and a enzyme-linked immunosorbent assay (ELISA), can be used, whereby intact biologically active GLP-1 and its metabolites can be detected. See, for example, Deacon et al. (1995) *Diabetes* 44:1126-1131. To illustrate, after GLP-1 administration, the intact peptide can be measured using an NH2-terminally directed RIA or ELISA, while the difference in concentration between these assays and a COOH-terminal-specific RIA allowed determination of NH2-terminally truncated metabolites. Without inhibitor, subcutaneous GLP-1 is rapidly degraded in a time-dependent manner, forming a metabolite which co-elutes on HPLC with GLP-I(9-36) amide and has the same immunoreactive profile. For instance, thirty minutes after subcutaneous GLP-1 administration to diabetic patients (n=8), the metabolite accounted for 88.5+ 1.9% of the increase in plasma immunoreactivity determined by the COOH-terminal RIA, which was higher than the levels measured in healthy subjects (78.4+3.2%; n=8; P<0.05). See Deacon et al., supra. Intravenously infused GLP-I was also extensively degraded.

D. Pharmaceutical Formulations

The inhibitors can be administered in various forms, depending on the disorder to be treated and the age, condition and body weight of the patient, as is well known in the art. For example, where the compounds are to be administered orally, they may be formulated as tablets, capsules, granules, powders or syrups; or for parenteral administration, they may be formulated as injections (intravenous, intramuscular or subcutaneous), drop infusion preparations or suppositories. For application by the ophthalmic mucous membrane route, they may be formulated as eyedrops or eye ointments. These formulations can be prepared by conventional means, and, if desired, the active ingredient may be mixed with any conventional additive, such as an excipient, a binder, a disintegrating agent, a lubricant, a corrigent, a solubilizing agent, a suspension aid, an emulsifying agent or a coating agent. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses.

Glucose metabolism can be altered, and symptoms associated with type I diabetes can be decreased or eliminated, in accordance with a "timed" administration of DPIV inhibitors wherein one or more appropriate indices for glucose metabolism and/or type I diabetes can be used to assess effectiveness of the treatment (dosage and/or timing): e.g. glucose tolerance, glucose level, insulin level, insulin sensitivity, glycosylated hemoglobin.

An effective time for administering DPIV inhibitors needs to be identified. This can be accomplished by routine experiment as described below, using one or more groups of animals (preferably at least 5 animals per group).

In animals, insulinotropic activity by DPIV inhibitor treatment can be assessed by administering the inhibitor at a particular time of day and measuring the effect of the administration (if any) by measuring one or more indices associated with glucose metabolism, and comparing the post-treatment values of these indices to the values of the same indices prior to treatment.

The precise time of administration and/or amount of DPIV inhibitor that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

While the subject is being treated, glucose metabolism is monitored by measuring one or more of the relevant indices at predetermined times during a 24-hour period. Treatment (amounts, times of administration and type of medication) may be adjusted (optimized) according to the results of such monitoring. The patient is periodically reevaluated to determine extent of improvement by measuring the same parameters, the first such reevaluation typically occurring at the end of four weeks from the onset of therapy, and subsequent reevaluations occurring every 4 to 8 weeks during therapy and then every 3 months thereafter. Therapy may continue for several months or even years with six months being a typical length of therapy for humans.

Adjustments to the amount(s) of drug(s) administered and possibly to the time of administration may be made based on these reevaluations. For example, if after 4 weeks of treatment one of the metabolic indices has not improved but at least one other one has, the dose could be increased by ⅓ without changing the time of administration.

Treatment can be initiated with smaller dosages which are less than the optimum dose of the compound. Thereafter, the dosage should be increased by small increments until the optimum effect under the circumstances is reached. For convenience, the total daily dosage may be divided and administered in portions during the day if desired.

The phrase "therapeutically effective amount" as used herein means that amount of, e.g., a DPIV inhibitor(s), which is effective for producing some desired therapeutic effect by inhibiting, for example, the proteolysis of a peptide hormone at a reasonable benefit/risk ratio applicable to any medical treatment.

The phrase "pharmaceutically acceptable" is employed herein to refer to those DPIV inhibitors, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically acceptable salts" refers to the relatively non-toxic, inorganic and organic acid addition salts of DPUV inhibitors. These salts can be prepared in situ during the final isolation and purification of the DPIV Inhibitors, or by separately reacting a purified DPIV inhibitor in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", J. Pharm. Sci. 66:1-19).

In other cases, the DPIV inhibitor useful in the methods of the present invention may contain one or more acidic functional groups and, thus, are capable of forming pharmaceutically acceptable salts with pharmaceutically acceptable bases. The term "pharmaceutically-acceptable salts" in these instances refers to the relatively non-toxic, inorganic and organic base addition salts of a DPIV inhibitor(s). These salts can likewise be prepared in situ during the final isolation and purification of the DPIV inhibitor(s), or by separately reacting the purified DPIV inhibitor(s) in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a DPIV inhibitor(s) with the carrier and, optionally, one or more accessory ingredients. In general, the formulations are prepared by uniformly and intimately bringing into association a DPIV inhibitor with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a DPIV inhibitor(s) as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active DPIV inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more DPIV inhibitor(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of a DPIV inhibitor(s) include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to DPIV inhibitor(s), excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a DPIV inhibitor(s), excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The DPIV inhibitor(s) can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a DPIV inhibitor(s) to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more DPIV inhibitor(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the, inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of DPIV inhibitor(s) in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the DPIV inhibitor(s) of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of agents may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrastemal injection and infusion.

The phrases "systemic administration," "administered systemically," "peripheral administration" and "administered peripherally" as used herein mean the administration of a DPIV inhibitor, drug or other material other than directly into the central nervous system, such that it enters the patient's system and, thus, is subject to metabolism and other like processes, for example, subcutaneous administration.

These DPIV inhibitor(s) may be administered to humans and other animals for therapy by any suitable route of administration, including orally, nasally, as by, for example, a spray, rectally, intravaginally, parenterally, intracistemally and topically, as by powders, ointments or drops, including buccally and sublingually.

Regardless of the route of administration selected, the DPIV inhibitor(s), which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

E. Conjoint Administration

Another aspect of the invention provides a conjoint therapy wherein one or more other therapeutic agents are administered with the protease inhibitor. Such conjoint treatment may be achieved by way of the simultaneous, sequential or separate dosing of the individual components of the treatment.

In one embodiment, a DPIV inhibitor is conjointly administered with immunosuppressive agents, such as, for example, cyclosporine; cyclosporine in conjunction with either azathioprine, steroids, or both; FK506 tacrolimus (Prograf); or mycophenolate mofetil (Cellcept).

iv. Business Methods

One aspect of the present invention relates to a kit comprising compounds as described herein, such as DPIV inhibitors, for treatment or prevention of autoimmune disorders, such as Type 1 diabetes, septic shock, multiple sclerosis, IBD or Crohn's disease in a patient, preferably a human, and in association with instructions (written and/or pictorial) describing the use of the formulation for treatment or prevention of autoimmune disorders, such as Type 1 diabetes, septic shock, multiple sclerosis, IBD or Crohn's disease, and optionally, warnings of possible side effects and drug-drug or drug-food interactions.

The invention further contemplates a method for conducting a pharmaceutical business, comprising: (a) manufacturing a pharmaceutical preparation comprising a sterile pharmaceutical excipient and compounds as described herein, such as DPIV inhibitors; and (b) marketing (e.g., providing promotional and/or informative presentations (such as displays, telemarketing, and lectures), products (such as trial samples of the preparation), and/or documentation (including leaflets, pamphlets, websites, posters, etc.)) to healthcare providers, such as doctors, hospitals, clinics, etc., a benefit of using the pharmaceutical preparation for treatment or prevention of autoimmune disorders, such as Type 1 diabetes, septic shock, multiple sclerosis, IBD or Crohn's disease.

Another aspect of the invention provides for a method for conducting a pharmaceutical business, comprising: (a) providing a distribution network for selling the pharmaceutical composition comprising a sterile pharmaceutical excipient and compounds as described herein, such as DPIV Inhibitors; and (b) providing instruction material to patients or physicians for using the pharmaceutical composition for treatment or prevention of autoimmune disorders, such as Type 1 diabetes, septic shock, multiple sclerosis, IBD or Crohn's disease.

Yet another aspect of the invention provides for a method for conducting a pharmaceutical business, comprising: (a) determining an appropriate pharmaceutical preparation and dosage of a compounds as described herein, such as DPIV inhibitors for treatment or prevention of autoimmune disorders, such as Type 1 diabetes, septic shock, multiple sclerosis, IBD or Crohn's disease; (b) conducting therapeutic profiling of the pharmaceutical preparation for efficacy and toxicity in animals; (c) providing a distribution network for selling a pharmaceutical composition having an acceptable therapeutic profile; and, optionally, (d) providing a sales group for marketing the preparation to healthcare providers.

EXEMPLIFICATION

The invention now being generally described, it will be more readily understood by reference to the following examples which are included merely for purposes of illustration of certain aspects and embodiments of the present invention, and are not intended to limit the invention.

Example 1

Synthesis of BoroProline

Referring to FIG. 1, the starting compound I is prepared essentially by the procedure of Matteson et al. (Organometallics 3:1284, 1984), except that a pinacol ester is substituted for the pinanediol ester. Similar compounds such as boropipecolic acid and 2-azetodine boronic acid can be prepared by making the appropriate selection of starting material to yield the pentyl and propyl analogs of compound I. Further, Cl can be substituted for Br in the formula, and other diol protecting groups can be substituted for pinacol in the formula, e.g., 2,3-butanediol and alphapinanediol.

Compound II is prepared by reacting compound I with $[(CH_3)O_3Si]_2N-Li^+$. In this reaction hexamethyldisilazane is dissolved in tetrahydrofuran and an equivalent of n-butyllithium added at −78° C. After warming to room temperature (20° C.) and cooling to −78° C., an equivalent of compound I is added in tetrahydrofuran. The mixture is allowed to slowly come to room temperature and to stir overnight. The alpha-bis[trimethylsilane]-protected amine is isolated by evaporating solvent and adding hexane under anhydrous conditions. Insoluble residue is removed by filtration under a nitrogen blanket, yielding a hexane solution of compound II.

Compound III, the N-trimethysilyl protected form of boroproline is obtained by the thermal cyclization of compound II during the distillation process in which compound II is heated to 100-150° C. and distillate is collected which boils 66-62° C. at 0.06-0.10 mm pressure.

Compound IV, boroproline-pinacol hydrogen chloride, is obtained by treatment of compound III with HCl:dioxane. Excess HCl and by-products are removed by trituration with ether. The final product is obtained in a high degree of purity by recrystallization from ethyl acetate.

The boroProline esters can also be obtained by treatment of the reaction mixture obtained in the preparation of compound II with anhydrous acid to yield 1-amino-4-bromobutyl boronate pinacol as a salt. Cyclization occurs after neutralizing the salt with base and heating the reaction.

Example 2

Preparation of BoroProline-Pinacol

The intermediate, 4-Bromo-1-chlorobutyl boronate pinacol, was prepared by the method in Matteson et al. (Organometallics 3:1284, 1984) except that conditions were modified for large scale preparations and pinacol was substituted for the pinanediol protecting group.

3-bromopropyl boronate pinacol was prepared by hydrogenboronation of allyl bromide (173 ml, 2.00 moles) with catechol borane (240 ml, 2.00 moles). Catechol borane was added to allyl bromide and the reaction heated for 4 hours at 100° C. under a nitrogen atmosphere. The product, 3-bromopropyl boronate catechol (bp 95-102° C., 0.25 mm), was isolated in a yield of 49% by distillation. The catechol ester (124 g, 0.52 moles) was transesterified with pinacol (61.5 g, 0.52 moles) by mixing the component in 50 ml of THF and allowing them to stir for 0.5 hours at 0° C. and 0.5 hours at room temperature. Solvent was removed by evaporation and 250 ml of hexane added. Catechol was removed as a crystalline solid. Quantitative removal was achieved by successive dilution to 500 ml and to 1000 ml with hexane and removing crystals at each dilution. Hexane was evaporated and the product distilled to yield 177 g (bp 60-64° C., 0.35 mm).

4-Bromo-1-chlorobutyl boronate pinacol was prepared by homologation of the corresponding propyl boronate. Methylene chloride (50.54 ml, 0.713 moles) was dissolved in 500 ml of THF, 1.54N n-butyllithium in hexane (480 ml, 0.780 moles) was slowly added at −100° C. 3-Bromopropyl boronate pinacol (178 g, 0.713 moles) was dissolved in 500 ml of THG, cooled to the freezing point of the solution, and added to the reaction mixture. Zinc chloride (54.4 g, 0.392 moles) was dissolved in 250 ml of THG, cooled to 0° C., and added to the reaction mixture in several portions. The reaction was allowed to slowly warm to room temperature and to stir overnight. Solvent was evaporated and the residue dissolved in hexane (1 liter) and washed with water (1 liter). Insoluble material was discarded. After drying over anhydrous magnesium sulfate and filtering, solvent was evaporated. The product was distilled to yield 147 g (bp 110-112° C., 0.200 mm).

N-Trimethylsilyl-boroProline pinacol was prepared first by dissolving hexamethyldisilizane (20.0 g, 80.0 mmoles) in 30 ml of THF, cooling the solution to −78° C., and adding 1.62N n-butyllithium in hexane (49.4 ml, 80.0 mmoles). The solution was allowed to slowly warm to room temperature. It was recooled to −78° C. and 4-bromo-1-chlorobutyl boronate pinacol (23.9 g, 80.0 mmoles) added in 20 ml of THF. The mixture was allowed to slowly warm to room temperature and to stir overnight. Solvent was removed by evaporation and dry hexane (400 ml) added to yield a precipitate which was removed by filbration under a nitrogen atmosphere. The filtrate was evaporated and the residue distilled, yielding 19.4 g of the desired product (bp 60-62° C., 0.1-0.06 mm).

H-boroProline-pinacol.HCl (boroProline-pinacol.HCl) was prepared by cooling N-trimethylsilyl-boroProline pinacol (16.0 g, 61.7 mmoles) to −78° C. and adding 4N HCL: dioxane 46 ml, 185 mmoles). The mixture was stirred 30 minutes at −78° C. and 1 hour at room temperature. Solvent was evaporated and the residue triturated with ether to yield a solid. The crude product was dissolved in chloroform and insoluble material removed by filtration. The solution was evaporated and the product crystallized from ethyl acetate to yield 11.1 g of the desired product (mp 156.5-157° C.).

Example 3

Synthesis of BoroProline Peptides

General methods of coupling of N-protected peptides and amino acids with suitable side-chain protecting groups to H-boroProline-pinacol are applicable. When needed, side-chain protecting and N-terminal protecting groups can be removed by treatment with anhydrous HCl, HBr, trifluoroacetic acid, or by catalytic hydrogenation. These procedures are known to those skilled in the art of peptide synthesis.

The mixed anhydride procedure of Anderson et al. (J. Am. Chem. Soc. 89:5012, 1984) is preferred for peptide coupling. Referring again to FIG. 1, the mixed anhydride of an N-protected amino acid or a peptide is prepared by dissolving the peptide in tetrahydrofuran and adding one equivalent of N-methylmorpholine. The solution is cooled to −20° C. and an equivalent of isobutyl chloroformate is added. After 5 minutes, this mixture and one equivalent of triethylamine (or other sterically hindered base) are added to a solution of H-boroPro-pinacol dissolved in either cold chloroform of tetrahydrofuran.

The reaction mixture is routinely stirred for one hour at −20° C. and 1 to 2 hours at room temperature (20° C.). Solvent is removed by evaporation, and the residue is dissolved in ethyl acetate. The organic solution is washed with 0.20N hydrochloric acid, 5% aqueous sodium bicarbonate, and saturated aqueous sodium chloride. The organic phase is dried over anhydrous sodium sulfate, filtered, and evaporated. Products are purified by either silica gel chromatography or gel permeation chromatography using Sephadex™ LH-20 and methanol as a solvent.

Previous studies have shown that the pinacol protecting group can be removed in situ by preincubation in phosphate buffer prior to running biological experiments (Kettner et al., J. Biol. Chem. 259:15106, 1984). Several other methods are also applicable for removing pinacol groups from peptides, including boroProline, and characterizing the final product. First, the peptide can be treated with diethanolamine to yield the corresponding diethanolamine boronic acid ester, which can be readily hydrolyzed by treatment with aqueous acid or a sulfonic acid substituted polystyrene resin as described in Kettner et al. (supra). Both pinacol and pinanediol protecting groups can be removed by treating with BC13 in methylene chloride as described by Kinder et al. (J. Med. Chem. 28:1917). Finally, the free boronic acid can be converted to the difluoroboron derivative (—BF2) by treatment with aqueous HF as described by Kinder et al. (supra).

Similarly, different ester groups can be introduced by reacting the free boronic acid with various di-hydroxy compounds (for example, those containing heteroatoms such as S or N) in an inert solvent.

Example 4

Preparation of H-Ala-boroPro

Boc-Ala-boroPro was prepared by mixed anhydride coupling of the N-Boc-protected alanine and H-boroPro prepared as described above. H-Ala-boroPro (Ala-boropro) was prepared by removal of the Boc protecting group at 0° C. in 3.5 molar excess of 4N HCl-dioxane. The coupling and deblocking reactions were performed by standard chemical reaction. Ala-boroPro has a $K_i$ for DP-IV of in the nanomolar range. Boc-blocked Ala-boroPro has no affinity for DP-IV.

The two diastereomers of Ala-boroPro-pinacol, L-Ala-D-boroPro-pinacol and L-Ala-L-boroPro-pinacol, can be partially separated by silica gel chromatography with 20% methanol in ethyl acetate as eluant. The early fraction appears by NMR analysis to be 95% enriched in one isomer. Because this fraction has more inhibits DP-IV to a greater extent than later fractions (at equal concentrations) it is probably enriched in the L-boroPro (L-Ala-L-boroPro-pinacol) isomer.

Example 5

Synthesis of Cyclohexylglycine BoroAla

Referring to FIG. 1, a solution of 515 mg (2.00 mmol) of Boc-L-2-(cyclohexyl)glycine 1 (Chem-Impex International), 587 mg (2.26 mmol) of HCl.boroAla pinane 2, 332 mg (2.46 mmol) of HOBT, and 671 µL (4.84 mmol) of triethylamine in 6 mL of anhydrous DMF was treated with 498 mg (2.60 mmol) of EDC, and the resulting solution stirred at room temperature under argon for 18 h. The reaction mixture was diluted with a 200 mL of 10% aqueous citric acid and the resulting mixture extracted with 2×100 mL of ethyl acetate. The combined extracts were washed with brine, dried (MgSO$_4$), filtered, and concentrated to give a clear oil. The crude oil was chromatographed over silica gel with ethyl acetate/hexane to give the product ester as a clear oil. The oil was then dissolved in hydrogen chloride in diethyl ether (1.0 M solution, 25 mL) and stirred for 48 hours at room temperature. The mixture was evaporated to dryness in vacuo and redissolved in 25 mL phenylboronic acid solution (244 mg, 2 mmol) at pH 2 (0.01 N HCl) and ether (25 mL). After stirring for 30 min, the ether layer was removed and replaced with fresh ether (25 mL). This step was repeated for four times.

The aqueous phase was then lyophilized and purified by HPLC to afford 170 mg (37%) of the target compound 3.

Example 6

DPIV Assays on Serum Samples From Rats

Experiments show that DPIV enzyme activity was significantly decreased in rats treated with Cyclohexylglycine-boroAla. See FIG. 7. Four rats were used in this experiment: two females (#3 and #9) and two males (#10 and #11). Blood and plasma samples were collected from rats 1 hour after being treated with Cyclohexylglycine-boroAla. The collected serum samples were evaluated for DPPIV activity of Cyclohexylglycine-boroAla as follows:
1. 2 mg of Ala-Pro-paranitroanalide (substrate) was dissolved in 20 ml 0.1 M HEPES pH 8, 0.14 M NaCl (buffer).
2. Serum samples were diluted into substrate solution in the wells of a microtiter plate. For each sample, 10 uL of serum was diluted into 150 µL of substrate.
3. A reading of the A410 in each well was recorded immediately after the dilution of serum into substrate, and again after approximately 1 hour. The time of data acquisition for each reading is recorded in the data file by the microplate reader software.

The rate of absorbance change was obtained by subtracting the first reading from the second and dividing by the reaction time to give DeltaA410/hr. The DPIV activity was plotted in units of DeltaA410 $hr^{-1} \mu^{-1}$.

Example 7

Incidence of Diabetes in NOD Mice Upon Treatment With DPIV Inhibitors

The experiment was started on 8-10 week old NOD mice. The mice were kept under VAF/SPF conditions and fed everyday with either Val-boro-Pro (0.034 mg/kg) or Cyclohexyl-boro-Ala (0.34 mg/kg) for 60 days and then observed for the development of spontaneous diabetes. The mice were tested for the excretion of sugar in urine and considered positive for diabetes when sugar was detected in the urine.

Figure 5:
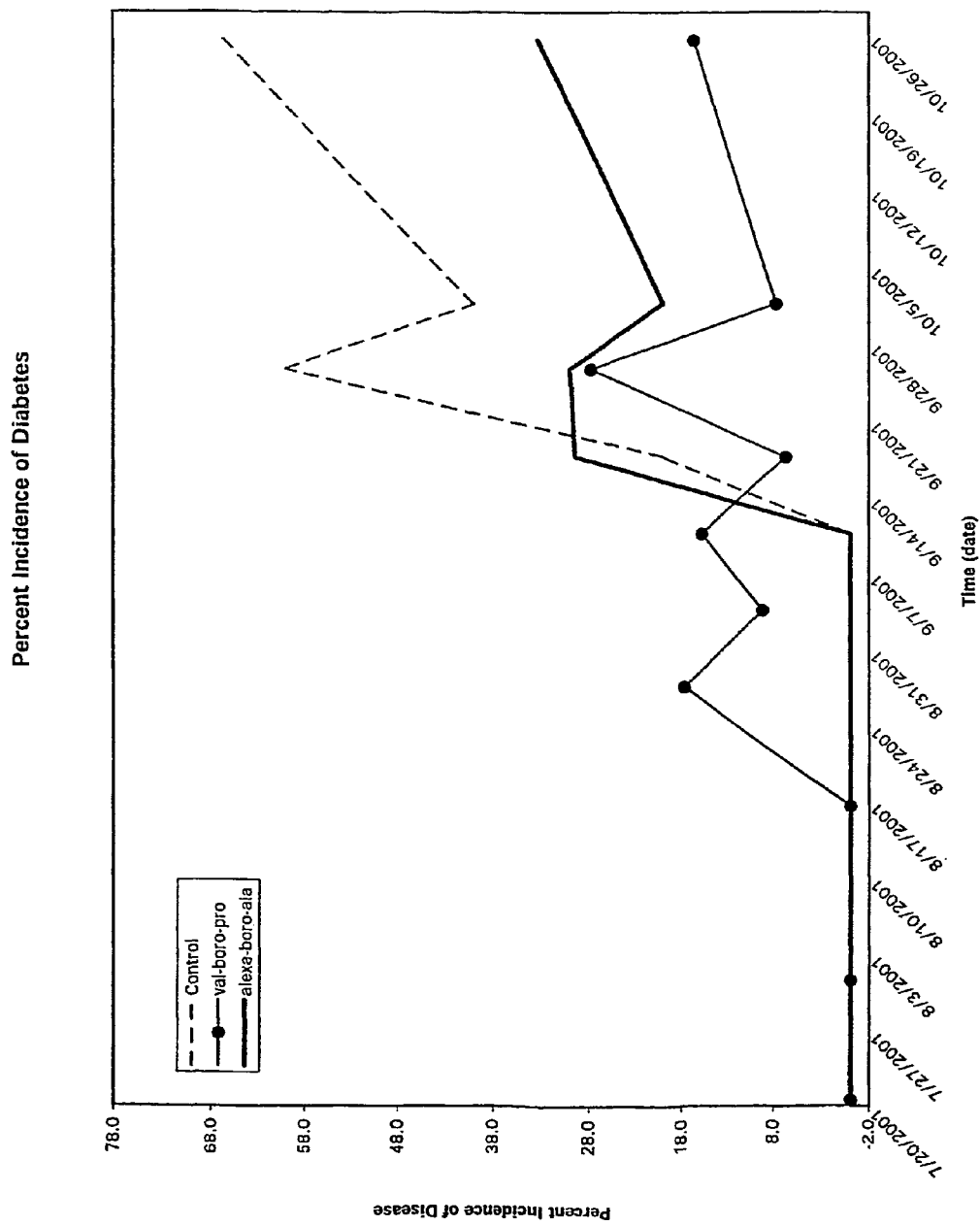
FIG. 5 is a time course of incidence of Type 1 diabetes in NOD mice upon administration of Val-boro-Pro, or Cyclohexylglycine-boro-Ala, as compared to control.
Figure 6:
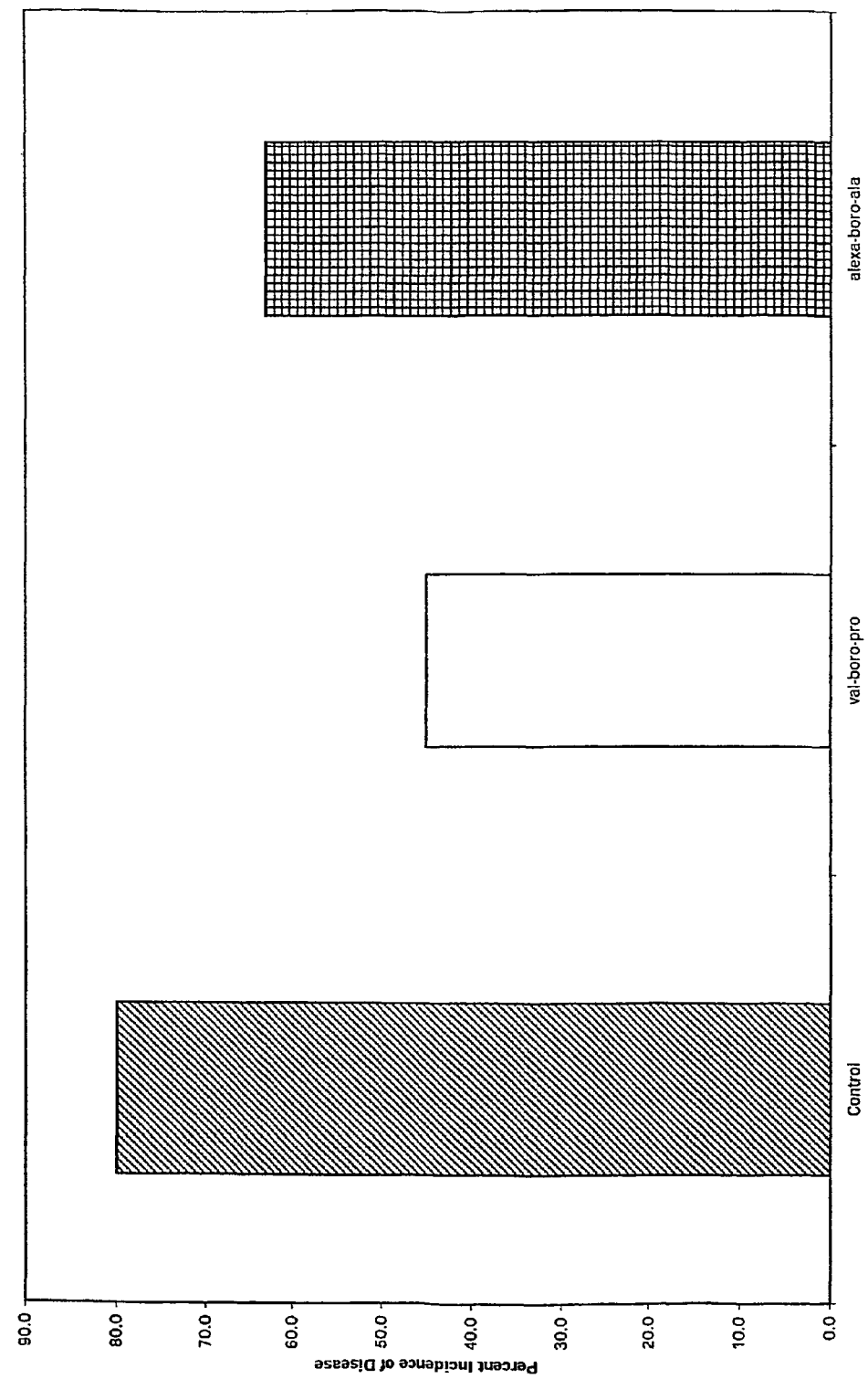
FIG. 6 is a bar graph illustrating the incidence of Type 1 diabetes in NOD mice upon administration of Val-boro-Pro or Cyclohexylglycine-boro-Ala, as compared to control at 120 days after start of treatment.

The graph shows cumulative incidence of Diabetes over time (FIG. 5). One of the interesting features of the NOD mice treated with Val-boro-Pro was that some of the mice that showed signs of diabetes got better and recovered. At the end of the experiment, the mice in Val-boro-Pro group not only had low incidence of Diabetes (FIG. 6) but also showed generally good health compared to the other groups.

All of the above-cited references and publications are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

The invention claimed is:

1. A method for treating an autoimmune disease in an animal, comprising administering to said animal a composition comprising one or more inhibitors of DPIV in an amount sufficient to suppress the immune system to treat said autoimmune disease, wherein said autoimmune disease is selected from the group consisting of multiple sclerosis, systemic lupus erythematosus (SLE), myasthenia gravis, Grave's disease, and type II collagen-induced arthritis; and said inhibitor of DPIV is represented by the formula:

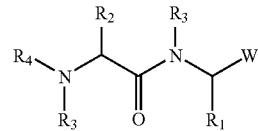

wherein
$R_1$ represents hydrogen, lower alkyl;
$R_2$ represents a branched lower alkyl, cycloalkyl, or cycloalkylalkyl;
$R_3$ represents hydrogen;
$R_4$ represents hydrogen, or a C-terminally linked naturally-occurring α-amino acid residue selected from the group consisting of glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan;
W represents

and
$Y_1$ and $Y_2$ are, independently, OH, or connected via a ring having from 5 to 8 atoms in a ring structure.

2. The method of claim 1, wherein the autoimmune disease is multiple sclerosis.
$R_{36}$ is lower alkyl and $R_{38}$ is hydrogen, or, $R_{36}$ and $R_{38}$ together form a 4-7 membered heterocycle; and
$R_{40}$ represents a C-terminally linked naturally-occurring α-amino acid residue selected from the group consisting of glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan.

3. The method of claim 1, wherein the inhibitor is orally active.

4. The method of claim 1, wherein

represents

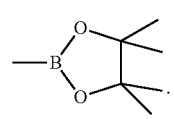

5. A method for treating an autoimmune disease in an animal, comprising administering to said animal a composition comprising one or more inhibitors of DPIV in an amount sufficient to suppress the immune system to treat said autoimmune disease, wherein said autoimmune disease is selected from the group consisting of multiple sclerosis, systemic lupus erythematosus (SLE), myasthenia gravis, Grave's disease, and type II collagen-induced arthritis; and said inhibitor of DPIV is represented by the formula:

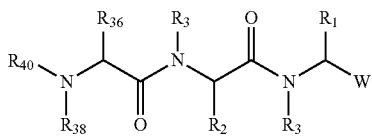

wherein:
$R_1$ represents hydrogen, lower alkyl;
$R_2$ represents a branched lower alkyl, cycloalkyl, or cycloalkylalkyl;
$R_3$ represents hydrogen;
W represents

and
$Y_1$ and $Y_2$ are, independently, OH, or connected via a ring having from 5 to 8 atoms in a ring structure;
$Y_1$ and $Y_2$ represent independently hydroxyl;
$R_2$ represents cyclohexyl; and
$R_3$ and $R_4$, represent, independently and for each occurrence, hydrogen.

6. The method of claim 1, wherein $R_1$ represents lower alkyl.

7. The method of claim 1, wherein $R_1$ represents methyl.

8. The method of claim 1, wherein $R_2$ is t-butyl or cyclohexyl.

9. The method of claim 1, wherein:
$R_1$ represents methyl;
$R_2$ represents cyclohexyl; and
$R_3$ and $R_4$ represent, independently and for each occurrence, hydrogen.

10. The method of claim 1, wherein the inhibitor is represented by the formula:

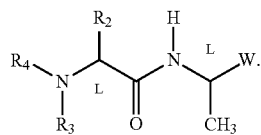

11. The method of claim 10, wherein:
W represents

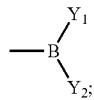

* * * * *

UNITED STATES PATENT AND TRADEMARK OFFICE
CERTIFICATE OF CORRECTION

PATENT NO. : 8,410,053 B2  
APPLICATION NO. : 10/496627  
DATED : April 2, 2013  
INVENTOR(S) : William W. Bachovchin et al.

Page 1 of 2

It is certified that error appears in the above-identified patent and that said Letters Patent is hereby corrected as shown below:

In the Claims

At column 44, claim number 2, line numbers 38 - 45, delete:

"$R_{36}$ is lower alkyl and $R_{38}$ is hydrogen, or, $R_{36}$ and $R_{38}$ together form a 4-7 membered heterocycle; and $R_{40}$ represents a C-terminally linked naturally-occurring α-amino acid residue selected from the group consisting of glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan."

At column 45, claim number 5, line numbers 30 - 33, replace:

"$Y_1$ and $Y_2$ represent independently hydroxyl;

$R_2$ represents cyclohexyl; and $R_3$ and $R_4$, represent, independently and for each occurrence, hydrogen."

with

--$R_{36}$ is lower alkyl and $R_{38}$ is hydrogen, or, $R_{36}$ and $R_{38}$ together form a 4-7 membered heterocycle; and $R_{40}$ represents a C-terminally linked naturally-occurring α-amino acid residue selected from the group consisting of glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan.--

Signed and Sealed this  
Twenty-fourth Day of June, 2014

Michelle K. Lee  
*Deputy Director of the United States Patent and Trademark Office*

At column 46, claim number 11, line number 30, insert:

--$Y_1$ and $Y_2$ represent independently hydroxyl;

$R_2$ represents cyclohexyl; and $R_3$ and $R_4$ represent, independently and for each occurrence, hydrogen.--